United States Patent
Swanzey et al.

(10) Patent No.: US 10,362,466 B2
(45) Date of Patent: Jul. 23, 2019

(54) METHODS AND APPARATUS FOR IMPROVED LOW ENERGY DATA COMMUNICATIONS

(71) Applicant: ASCENSIA DIABETES CARE HOLDINGS AG, Basel (CH)

(72) Inventors: Todd Swanzey, Putnam Valley, NY (US); Greg R. Stefkovic, Mahopac, NY (US); Qiang Fu, Briarcliff Manor, NY (US); Mu Wu, Hopewell Junction, NY (US)

(73) Assignee: Ascensia Diabetes Care Holdings AG, Basel (CH)

( * ) Notice: Subject to any disclaimer, the term of this patent is extended or adjusted under 35 U.S.C. 154(b) by 0 days.

(21) Appl. No.: 15/324,654

(22) PCT Filed: Oct. 27, 2014

(86) PCT No.: PCT/US2014/062404
§ 371 (c)(1),
(2) Date: Jan. 6, 2017

(87) PCT Pub. No.: WO2016/007186
PCT Pub. Date: Jan. 14, 2016

(65) Prior Publication Data
US 2017/0201931 A1 Jul. 13, 2017

Related U.S. Application Data

(60) Provisional application No. 62/021,690, filed on Jul. 7, 2014.

(51) Int. Cl.
*H04B 7/00* (2006.01)
*H04L 29/06* (2006.01)
(Continued)

(52) U.S. Cl.
CPC .............. *H04W 4/80* (2018.02); *A61B 5/002* (2013.01); *A61B 5/14532* (2013.01);
(Continued)

(58) Field of Classification Search
CPC ..... H04W 4/008; H04W 48/10; H04W 76/00; H04W 76/02; H04W 72/1221; H04W 84/12; H04L 65/4076
(Continued)

(56) References Cited

U.S. PATENT DOCUMENTS 6,540,672 B1 * 4/2003 Simonsen .......... A61B 5/14532
128/903
6,569,094 B2 5/2003 Suzuki et al.
(Continued)

FOREIGN PATENT DOCUMENTS

| CN | 102565413 A | 7/2012 |
|---|---|---|
| CN | 202838653 U | 3/2013 |

(Continued)

OTHER PUBLICATIONS

International Search Report and Written Opinion of related International Application No. PCT/US14/69628 dated Mar. 11, 2015.
(Continued)

*Primary Examiner* — Quochien B Vuong
(74) *Attorney, Agent, or Firm* — Dugan & Dugan, PC

(57) ABSTRACT

Embodiments include determining a reference value on a first device; broadcasting the reference value from the first device; connecting the first device to a second device if the second device requests data from the first device; transmitting any new data if the second device requests data from the first device; generating and broadcasting a new reference value if the first device has new data; broadcasting the reference value from the first device again if the first device does not have new data; receiving a reference value in the
(Continued)

second device from the first device; and if the received reference value does not match the stored reference value then transmitting a request from the second device for new data from the first device, receiving new data from the first device into the second device, and storing the received reference value as a new stored reference value. Numerous other aspects are provided.

20 Claims, 16 Drawing Sheets

(51) Int. Cl.

| | | |
|---|---|---|
| H04W 4/80 | (2018.01) | |
| H04W 76/10 | (2018.01) | |
| H04W 4/20 | (2018.01) | |
| H04W 4/02 | (2018.01) | |
| H04W 4/60 | (2018.01) | |
| G06F 3/01 | (2006.01) | |
| H04M 1/725 | (2006.01) | |
| H04W 12/08 | (2009.01) | |
| A61B 5/00 | (2006.01) | |
| A61B 5/145 | (2006.01) | |
| H04W 48/10 | (2009.01) | |
| H04L 29/08 | (2006.01) | |
| H04W 4/06 | (2009.01) | |
| H04W 84/18 | (2009.01) | |
| H04W 8/00 | (2009.01) | |
| H04W 48/16 | (2009.01) | |
| H04W 74/00 | (2009.01) | |

(52) U.S. Cl.
CPC .......... *G06F 3/016* (2013.01); *H04L 63/0869* (2013.01); *H04L 63/0876* (2013.01); *H04L 63/107* (2013.01); *H04M 1/7253* (2013.01); *H04W 4/023* (2013.01); *H04W 4/027* (2013.01); *H04W 4/20* (2013.01); *H04W 4/60* (2018.02); *H04W 12/08* (2013.01); *H04W 48/10* (2013.01); *H04W 76/10* (2018.02); *H04L 67/16* (2013.01); *H04M 2201/18* (2013.01); *H04M 2201/26* (2013.01); *H04M 2250/02* (2013.01); *H04M 2250/22* (2013.01); *H04W 4/06* (2013.01); *H04W 8/005* (2013.01); *H04W 48/16* (2013.01); *H04W 74/002* (2013.01); *H04W 84/18* (2013.01)

(58) Field of Classification Search
USPC ..... 455/3.01, 41.1, 41.2, 41.3, 414.1, 414.3; 370/312, 389, 390
See application file for complete search history.

(56) References Cited

U.S. PATENT DOCUMENTS

| | | | |
|---|---|---|---|
| 6,604,050 B2 | 8/2003 | Trippel et al. | |
| 6,607,484 B2 | 8/2003 | Suzuki et al. | |
| 6,790,178 B1 | 9/2004 | Mault et al. | |
| 6,819,013 B2 | 11/2004 | Kelly et al. | |
| 6,870,475 B2 | 3/2005 | Fitch et al. | |
| 7,286,894 B1 | 10/2007 | Grant et al. | |
| 7,316,648 B2 | 1/2008 | Kelly et al. | |
| 7,549,961 B1 | 6/2009 | Hwang | |
| 8,005,465 B2 * | 8/2011 | Salokannel | G06Q 30/02 455/414.1 |
| 8,131,564 B2 * | 3/2012 | Dicks | A61B 5/0022 600/300 |
| 8,135,014 B2 * | 3/2012 | Choi | G06Q 30/0225 370/392 |
| 8,483,974 B2 | 7/2013 | Connolly | |
| 8,579,813 B2 | 11/2013 | Causey et al. | |
| 8,682,598 B2 | 3/2014 | Connolly et al. | |
| 8,895,316 B2 | 11/2014 | Batman et al. | |
| 8,954,007 B2 * | 2/2015 | Hillyard | H04W 8/005 455/41.1 |
| 9,462,623 B2 * | 10/2016 | Jakusovszky | H04W 8/005 |
| 9,696,980 B2 * | 7/2017 | Dicks | G06F 8/63 |
| 2006/0009697 A1 | 1/2006 | Banet et al. | |
| 2006/0106433 A1 | 5/2006 | Mazar et al. | |
| 2007/0003061 A1 | 1/2007 | Jung et al. | |
| 2007/0027388 A1 | 2/2007 | Chou | |
| 2007/0181425 A1 | 8/2007 | Kim | |
| 2007/0293910 A1 | 12/2007 | Strother et al. | |
| 2007/0299480 A1 | 12/2007 | Hill | |
| 2008/0092638 A1 | 4/2008 | Brenneman et al. | |
| 2008/0109302 A1 | 5/2008 | Salokannel et al. | |
| 2009/0069642 A1 | 3/2009 | Gao et al. | |
| 2009/0116479 A1 | 5/2009 | Choi | |
| 2009/0243791 A1 | 10/2009 | Partin | |
| 2010/0000862 A1 | 1/2010 | Rao | |
| 2010/0113897 A1 | 5/2010 | Brenneman et al. | |
| 2010/0228111 A1 | 9/2010 | Friman | |
| 2011/0165865 A1 | 7/2011 | Gao et al. | |
| 2011/0256024 A1 | 10/2011 | Cole et al. | |
| 2012/0019379 A1 | 1/2012 | Ben Ayed | |
| 2012/0123227 A1 | 5/2012 | Sun et al. | |
| 2014/0149742 A1 | 5/2014 | Yau | |
| 2014/0266607 A1 | 9/2014 | Olodort | |
| 2014/0364056 A1 | 12/2014 | Belk | |
| 2016/0337448 A1 | 11/2016 | Gofman et al. | |

FOREIGN PATENT DOCUMENTS

| | | |
|---|---|---|
| CN | 205006870 U | 2/2016 |
| EP | 2741 528 | 6/2014 |
| WO | WO0152727 | 7/2001 |
| WO | WO 2008/153825 | 12/2008 |
| WO | WO 2009/006486 | 1/2009 |
| WO | WO 2015/157582 | 10/2015 |
| WO | WO 2016/007186 | 1/2016 |
| WO | WO 2016/007187 | 1/2016 |
| WO | WO 2016/007188 | 1/2016 |

OTHER PUBLICATIONS

International Search report of related International Application No. PCT/US2014/062404 dated Mar. 5, 2015.
International Search Report and Written Opinion of related International Application No. PCT/US2014/062433 dated Mar. 23, 2015.
Mare, Shrirang, et al. "ZEBRA: Zero-Effort Bilateral Recurring Authentication", 2014 IEEE Symposium on Security and Privacy, IEEE, May 18, 2014, pp. 705-720.
Mayrhofer, R., et al., "Shake Well before Use: Intuitive and Securing Pairing of Mobile Devices", IEEE Transactions on Mobile Computing, IEEE Service Center, Los Alamitos, CA, US, vol. 8, No. 6, 1 Jun. 2009, pp. 792-806.
International Search Report and Written Opinion of related International Application No. PCT/US2014/062472 dated Mar. 23, 2015.
International Search Report and Written Opinion of related International Application No. PCT/US2015/025213 dated Jun. 15, 2015.
International Preliminary Report on Patentability of related International Application No. PCT/US14/69628 dated Jul. 21, 2016.
International Preliminary Report on Patentability of related International Application No. PCT/US2015/025213 dated Oct. 20, 2016.
International Preliminary report on Patentability of related International Application No. PCT/US2014/062404 dated Jan. 19, 2017.
International Preliminary Report on Patentability of related International Application No. PCT/US2014/062472 dated Jan. 19, 2017.
International Preliminary Report on Patentability of related International Application No. PCT/US2014/062433 dated Jan. 19, 2017.

* cited by examiner

METHODS AND APPARATUS FOR IMPROVED LOW ENERGY DATA COMMUNICATIONS

RELATED APPLICATIONS

The present application claims priority to U.S. Provisional Patent Application Ser. No. 62/021,690, filed Jul. 7, 2014 and entitled "METHODS AND APPARATUS FOR IMPROVED DATA COMMUNICATIONS", which is hereby incorporated herein by reference in its entirety for all purposes.

FIELD

Embodiments of the present invention relate to communication between wireless electronic devices and, more specifically, to efficiently and securely establishing communication and exchanging data between such devices.

BACKGROUND

Bluetooth® Low Energy (BLE) or Bluetooth LE, marketed as Bluetooth Smart and included as part of the Bluetooth 4.0 standard, is a wireless personal area network technology designed and marketed by the Bluetooth Special Interest Group (SIG) aimed at novel applications in the healthcare, fitness, security, and home entertainment industries. Compared to the original Bluetooth protocol, BLE is intended to provide considerably reduced power consumption and cost while maintaining a similar communication range. The Bluetooth SIG defines several profiles (e.g., specifications for how a device works in a particular application) for low energy devices. Manufacturers implement the appropriate specification for their device in order to ensure compatibility. A single device may contain implementations of multiple profiles. Current low energy application profiles are based on the generic attribute (GATT) profile, a general specification for sending and receiving short pieces of data known as attributes over a low energy link. Bluetooth 4.0 provides low power consumption with higher bit rates but even more efficient communications between wireless electronic devices, particularly portable devices that operate on battery power, is desirable to improve the available run time for a battery cycle. Thus, what are needed are improvements or extensions to existing wireless protocols that make data communication more efficient.

SUMMARY

In some embodiments, a method of low energy communications is provided. The method includes determining a reference value on a first device; broadcasting the reference value from the first device; connecting the first device to a second device if the second device requests data from the first device; transmitting any new data if the second device requests data from the first device; generating and broadcasting a new reference value if the first device has new data; broadcasting the reference value from the first device again if the first device does not have new data; receiving a reference value in the second device from the first device; waiting for a new reference value if the received reference value matches a stored reference value; transmitting a request from the second device for new data from the first device if the received reference value does not match the stored reference value; receiving new data from the first device into the second device if the received reference value does not match the stored reference value; and storing the received reference value as a new stored reference value if the received reference value does not match the stored reference value.

In some embodiments, a system of low energy communications is provided. The system includes a first device; and a second device, wherein the first device includes a controller having memory operative to store instructions executable on the controller, the instructions operative to: determine a reference value on the first device, broadcast the reference value from the first device, connect the first device to the second device if the second device requests data from the first device, transmit any new data if the second device requests data from the first device, generate and broadcast a new reference value if the first device has new data, and broadcast the reference value from the first device again if the first device does not have new data. The second device includes a controller having memory operative to store instructions executable on the controller, the instructions operative to: receive a reference value in the second device from the first device, wait for a new reference value if the received reference value matches a stored reference value, transmit a request from the second device for new data from the first device if the received reference value does not match the stored reference value, receive new data from the first device into the second device if the received reference value does not match the stored reference value, and store the received reference value as a new stored reference value if the received reference value does not match the stored reference value.

In some embodiments, a wireless device for low energy communications is provided. The wireless device includes a controller; and a memory coupled to the controller, the memory operative to store instructions executable on the controller and operative to: determine a reference value; broadcast the reference value; and connect to a smart device if the smart device requests new data from the wireless device after receiving the broadcast reference value and determining that the broadcast reference value does not match a stored reference value.

In some embodiments, a method of improving data communications is provided. The method includes storing a characteristic of data transmitted from a first wireless electronic device to a second wireless electronic device, the characteristic of data transmitted being stored in the second device; broadcasting, from the first device, a characteristic of data to be transmitted by the first device; receiving the broadcasted characteristic of data to be transmitted at the second device; comparing, in the second device, the received broadcasted characteristic of data to be transmitted with the stored characteristic of data transmitted; and requesting a subsequent data transfer if the received broadcasted characteristic of data to be transmitted does not match the stored characteristic of data transmitted and not requesting a subsequent data transfer if the received broadcasted characteristic of data to be transmitted does match the stored characteristic of data transmitted.

In some embodiments, a method of pairing two wireless devices is provided. The method includes placing a smart device and a peripheral device in pairing mode; detecting at least one pairing motion event with a dual use piezo circuit within the peripheral device; transmitting an indication of the occurrence of the at least one pairing motion event to the smart device; receiving in the smart device the indication of the occurrence of the at least one pairing motion event in satisfaction of at least one pairing condition; and pairing the smart device with the peripheral device in response to satisfaction of the at least one pairing condition.

In some other embodiments, a system for pairing two wireless devices is provided. The system includes a first wireless device that includes a programmable smart device that is Bluetooth Low Energy (BLE) enabled; and a second wireless device that includes a BLE enabled peripheral device and a dual use piezo circuit within the peripheral device. The second wireless device includes a processor and memory storing peripheral device instructions executable on the processor, wherein the peripheral device instructions when executed are operable to: place the second wireless device in a pairing mode, detect performance of at least one pairing motion event, and broadcast an indication of the occurrence of the at least one pairing motion event to the smart device. The smart device includes a processor and memory storing smart device instructions executable on the processor, wherein the smart device instructions when executed are operable to: receive the indication of the occurrence of the at least one pairing motion event in satisfaction of at least one pairing condition, and pair the smart device and the peripheral device in response to satisfaction of the at least one pairing condition.

In yet other embodiments, a dual use piezo circuit is provided. The dual use piezo circuit includes a microcontroller including a comparator and a digital to analog converter (DAC); and a piezoelectric buzzer having outputs coupled to inputs of the microcontroller. An output of the DAC is coupled to an input of the comparator, and an output of the piezoelectric buzzer is coupled to an input of the comparator.

In some embodiments, a method of pairing two wireless devices is provided. The method includes placing at least one of two devices in a pairing mode; performing at least one pairing motion event with at least one of the wireless devices to satisfy at least one pairing condition; detecting satisfaction of the at least one pairing condition; and pairing the two wireless devices in response to detecting satisfaction of the at least one pairing condition.

In some other embodiments, a system for pairing two wireless devices is provided. The system includes a first wireless device that includes a programmable smart device that is Bluetooth Low Energy (BLE) enabled; and a second wireless device that is BLE enabled. The second wireless device includes a processor and memory storing second wireless device instructions executable on the processor, wherein the second wireless device instructions when executed are operable to place the second wireless device in a pairing mode. The smart device includes a processor and memory storing smart device instructions executable on the processor, wherein the smart device instructions when executed are operable to: detect performance of at least one pairing motion event, determine if performance of at least one pairing motion event satisfied at least one pairing condition, and pair the two wireless devices in response to determining satisfaction of the at least one pairing condition.

In yet other embodiments, a method of pairing two wireless devices is provided. The method includes executing a pairing application on a smart device that is BLE enabled; placing a second BLE enabled device immediately proximate to the smart device; placing the second device in a pairing mode; instructing a user to move the second device away from the smart device; instructing the user to move the second device toward the smart device in response to detecting that a first pairing condition has been satisfied by a first motion event; and pairing the smart device with the second device in response to detecting that a second pairing condition has been satisfied by a second motion event.

Numerous other aspects are provided in accordance with these and other aspects of the invention. Other features and aspects of the present invention will become more fully apparent from the following detailed description, the appended claims and the accompanying drawings.

DETAILED DESCRIPTION

Figure 1:
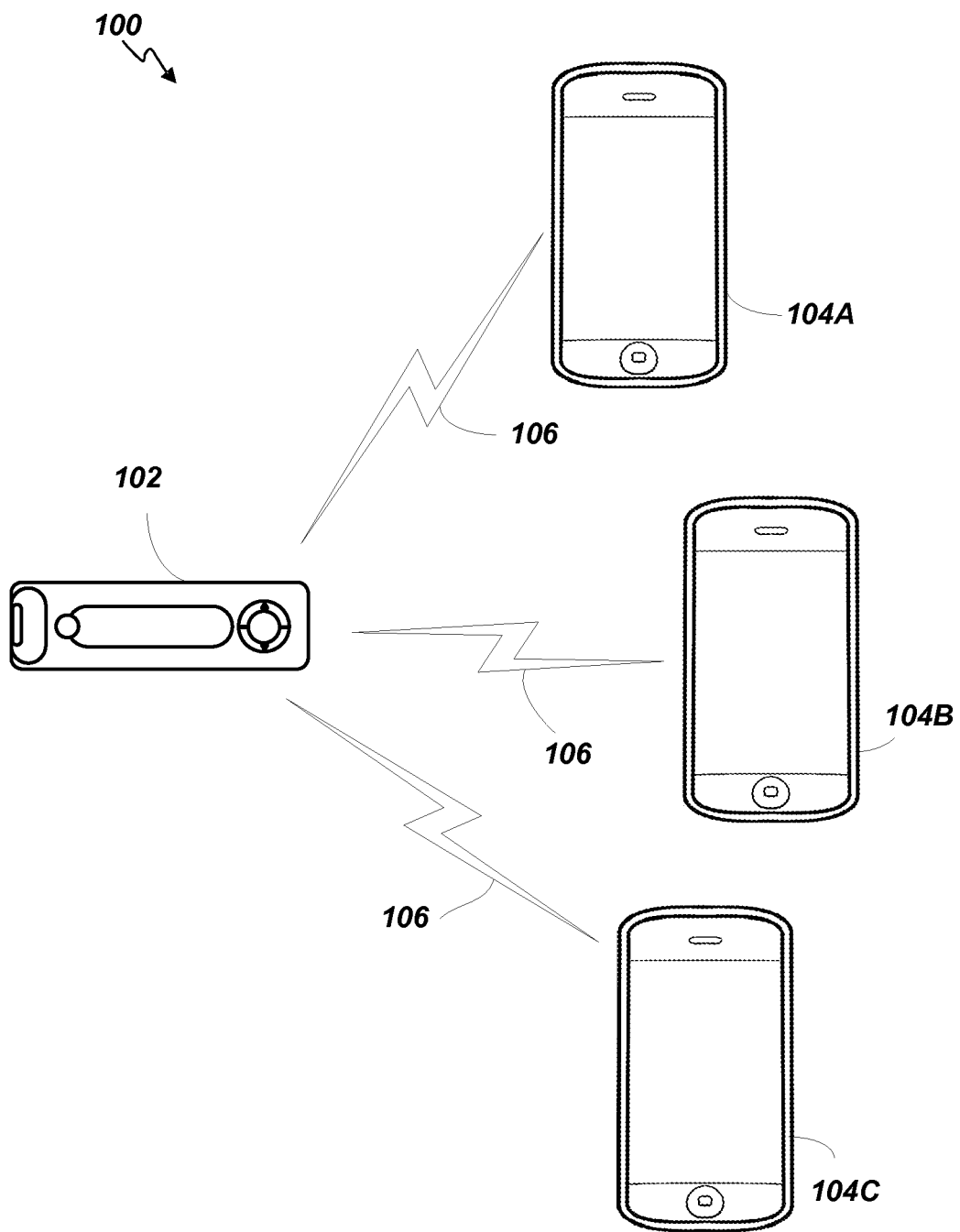
FIG. 1 depicts an example system diagram according to embodiments of the present invention.

Embodiments of the present invention provide improved methods and apparatus for conserving energy in wireless devices by only establishing a data transmission connection if new data is actually available to be transmitted. In other words, embodiments include securely determining if a wireless device has new data to transmit to another receiving device before expending the energy to connect the two paired devices. In some embodiments, a state variable value is included in the wireless device's BLE advertising data broadcasts and the receiving device stores the state variable value. If the value is not the same as a previously stored value, the receiving device assumes that there is new data available and proceeds with connecting the devices to allow transfer of the new data. If the value is the same as the previous value, this indicates that no new data is available and the system saves energy by not connecting the devices. In some embodiments, a counter (e.g., an incrementally increasing value) is used as the state variable, in some other embodiments, a random number is used, and in yet still other embodiments, a data characteristic related to the new data is used as the state variable. As long as the state variable value in the BLE advertising data broadcast changes to a value different than the previous value whenever new data is available, any of the above alternatives can be used.

Various wireless protocols such as BLE require a pairing process before establishing a communications link. BLE is a radio frequency (RF) communications protocol that operates in the 2.4 GHz industrial, scientific and medical (ISM) radio band. The BLE specification includes profile definitions to support communication between devices such as blood glucose meters (BGMs) and a smartphone or tablet, as well as a proximity profile that allows a proximity monitor (e.g., on a smartphone) to detect whether a proximity reporter (e.g., on a BGM) is within a specified range. Physical proximity can be estimated using the radio receiver's received signal strength indicator (RSSI) value.

Alternative embodiments of the present invention provide a novel pairing process that can be used to securely initiate a communications link between two devices without requiring a user to enter a key, nor the devices to include facilities for selecting, displaying and/or entering a key. In some embodiments, pairing is performed by putting the devices in pairing mode, moving the devices apart and then together. Using proximity measurement over time (e.g., using the proximity profile for BLE), a communications link can be established based upon first detecting the close proximity of the two devices, then detecting the increasing distance between the devices to a first threshold (e.g., reduced signal strength), and finally detecting the decreasing distance between the device to a second threshold (e.g., increased signal strength).

In some other embodiments, pairing is performed by putting the devices in pairing mode and then tapping the two devices together. The tap can be detected using an accelerometer (e.g., on a smart phone). In yet other embodiments, both discovery and pairing are achieved by taping one device that is in pairing mode with another device that is in a standby mode. The tap event is used to wake the device in standby mode to enter into pairing mode. With both devices in pairing mode, the pairing based on the tap event then proceeds as above.

In embodiments that use a tap event as the basis for pairing, an alternative means for detecting the tap event that can be used in place of (or in addition to) the wireless device's accelerometer is the wireless device's piezoelectric acoustic component. The Piezo speaker or buzzer found in many wireless devices is typically used to generate audio signals (i.e., sounds) but according to embodiments of the present invention, the piezoelectric acoustic component can additionally be used as a vibration, shock, or impact sensor to detect a tap event. Thus, in devices that do not have an accelerometer but do have some form of a piezoelectric acoustic component, such as a piezoelectric buzzer or piezoelectric speaker, the piezoelectric acoustic component can be used in the tap-based pairing methods of embodiments of the present invention while still being functional for generating audio.

In each type of the above embodiments, detection of a pre-defined physical motion event (e.g., a changing proximity pattern/motion sequence or a tap event that satisfies at least one pairing condition) while in pairing mode (or upon waking into pairing mode) serves to replace a conventional numeric key exchange process as the basis for securely initiating an established communications link between the two devices. Note that the establishment of the communications link is considered "secure" because only the two devices concurrently undergoing the pre-defined physical event while in pairing mode can establish the link. Eavesdropper devices are precluded from connecting (e.g., by high jacking the connection) because they do not participate in the pre-defined physical motion event (e.g., the tap event or the pairing motion sequence/proximity pattern). In other words, a non-secure pairing system would allow a link to be established by merely putting the two devices in pairing mode within range of each other. Embodiments of the present invention insure that only the intended devices that satisfy a pairing condition by participating in a pairing motion event can be paired and any eavesdropper devices cannot be paired. Thus, these embodiments provide the user with both the convenience of a simple, intuitive pairing procedure and a sense of security and certainty.

Turning to FIG. 1, an example system 100 according to embodiments of the present invention is provided. In some embodiments, the system 100 can include a BGM 102 with BLE capability and one or more smartphones 104A, 104B, 104C also with BLE capability. Note that the example system 100 is shown with a BGM 102 and one or more smartphones 104A, 104B, 104C merely as an illustrative example. Further note that the system 100 can alternatively use any wireless devices that are enabled with any communications protocol (e.g., BLE, Bluetooth, ANT Protocol, etc.) that uses pairing, bonding, or imprinting to securely establish a trusted wireless communication link 106. For example, embodiments of the present invention can be used for pairing Bluetooth devices such as the Lockitron Deadbolt, Motorola's H19TXT Headset, the Polaroid Pogo Connect Smart Pen, the Pebble E-Paper Watch, the Wahoo Fitness KICKR stationary exercise bike system, the Nike Hyperdunk+ basketball shoes, the Jabra Solemate docking station speaker system, the Withings Wireless Scale WS-30, the Scosche RHYTHM armband pulse sensor, the Microsoft Sculpt Mobile Keyboard, the Polaroid PoGo Instant Mobile Printer, the Kensington Vo200 Bluetooth Internet Phone, the BlueAnt Supertooth 3 Hands-Free Speakerphone, the Interlink Electronics VP6600 ExpressCard Media Remote for Bluetooth, the Lego Mindstorms NXT Robot Kit, the Baracoda D-Fly Bar Code Scanner, the GARMIN GLO Portable Aviation GPS. In addition, "smart devices" such as smartphones, tablets such as the Apple iPad, any personal or laptop computer with a Bluetooth adapter such as the Kinivo BTD-400 Bluetooth 4.0 USB adapter, any programmable device with wireless communication facility, etc. can be paired using the methods and apparatus of embodiments of the present invention.

Figure 2:
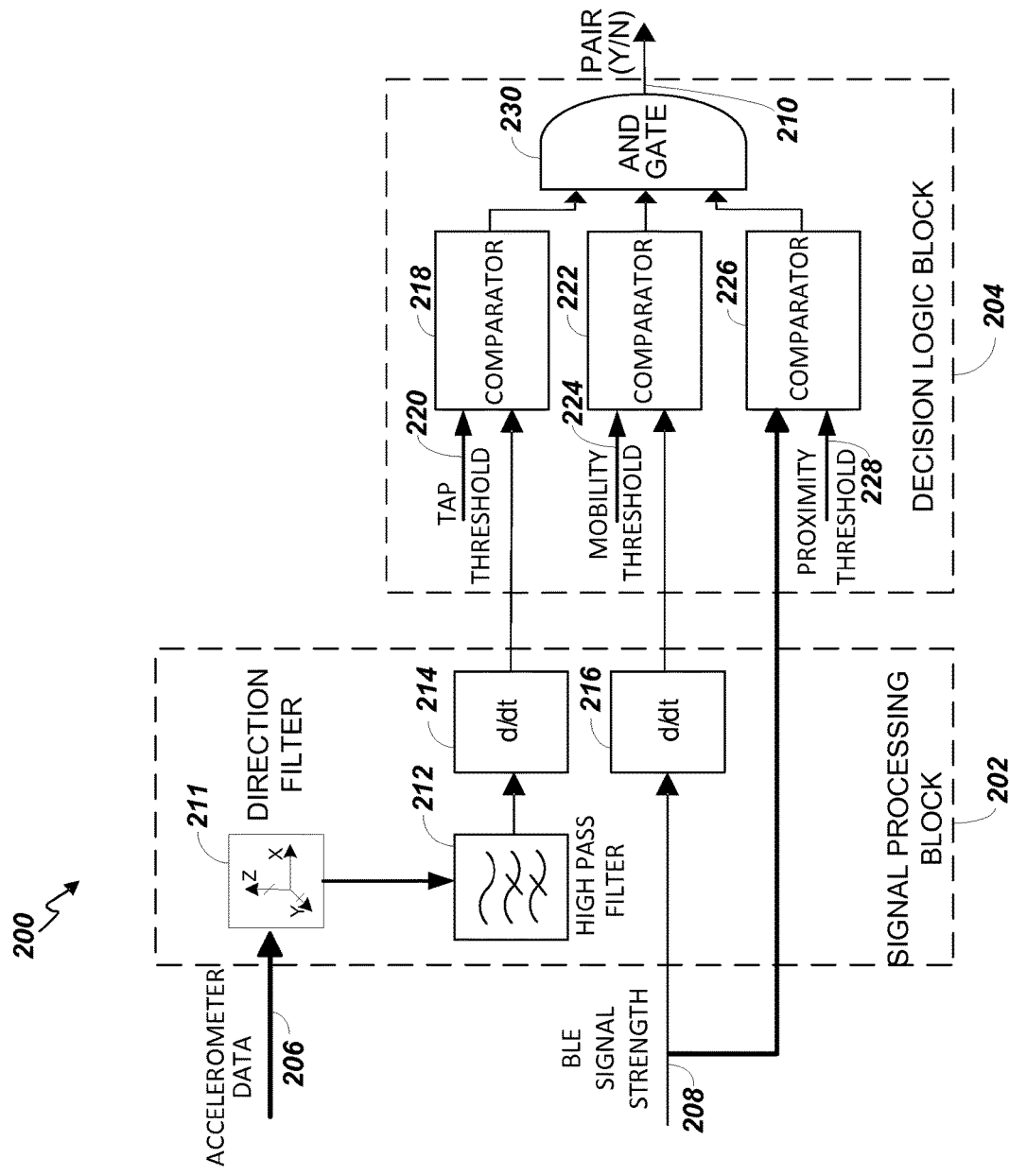
FIG. 2 depicts a functional block diagram of a first example logic circuit according to embodiments of the present invention.

FIG. 2 depicts a functional block diagram illustrating an example logic circuit 200 embodiment of the present invention that uses a tap event for pairing. Note that even though the components of the circuit 200 are represented as hardware devices, in some embodiments, circuit can be embodied as software or a combination of hardware and software components executing on a programmable device (e.g., a smartphone, tablet, etc.). The illustrated embodiment assumes that at least one of the two devices to be paired includes an accelerometer. The example circuit 200, in some embodiments, will only pair the devices if the following three pairing conditions are met. First, the tap is intense enough to yield an accelerometer response above a specified "tap threshold." Second, the RF signal strength is increasing (e.g., devices are getting closer) at a rate above a specified "mobility threshold." Third, the RF signal strength is at a value above a specified "proximity threshold." In some other embodiments, not all three pairing conditions are required to be satisfied for pairing.

In operation, assume that one of the devices to be paired is a BLE enabled smartphone 104A (FIG. 1) that has an accelerometer installed while the other device is a BLE enabled BGM 102. Embodiments of the present invention allow a user to pair the BLE BGM 102 with a smartphone 104A using an installed application and a simple tap to pair procedure. The user starts the application on the smartphone 104A and turns on the BGM 102. The user brings the devices together and taps one against the other. Discovery and pairing will be automatically initiated in response to the sudden change in the accelerometer readings and the proximity of the devices (i.e., a detected change in the BGM 102 BLE signal strength detected by application running on the smartphone 104A).

Thus, embodiments of the invention allow two BLE enabled devices to pair (in terms of the BLE standard) when one device taps another and the pairing conditions are satisfied. As illustrated in the functional block diagram of the logic circuit 200 in FIG. 2, meeting the pairing conditions can be represented as a signal flow gated by the conditions. The example logic circuit 200 is divided into a signal processing block 202 and a decision logic block 204. The signal processing block 202 receives an accelerometer data input signal 206 from the accelerometer and a BLE signal strength signal 208 from the BLE radio receiver. Based on these two input signals and three pre-defined threshold values, the logic circuit 200 creates a binary output signal 210 that indicates whether to pair the devices or not.

The signal processing block 202 determines if sudden changes in acceleration of the smartphone 104A have occurred that indicate a tap event has occurred. In some embodiments, the accelerometer data input signal 206 is initially put through a direction filter 211 to remove components of acceleration in the Y and Z directions. In order to detect the very moment when one device taps another (e.g., instantaneous motion), common "not so sudden" movements (which can be viewed as a low frequency component of the accelerometer data input signal 206) are filtered out from the data generated by the accelerometer. The low frequency component is filtered out by applying a high pass digital filter 212 to the accelerometer data input signal 206. In some embodiments, the high pass digital filter 212 can be embodied as a simple, 1-tap infinite impulse response (IIR) digital filter. This approach also helps to dampen or flatten out effects of gravity on sensor data since the accelerometer measures acceleration associated with the phenomenon of weight experienced by any test mass at rest in the frame of reference of the accelerometer device (e.g., commonly referred to as g-force acceleration).

The physics of a tap event is such that the devices experience some acceleration in the opposite direction (e.g., away from each other) immediately after the tap event. Thus, by taking the derivative of the high pass digital filter 212 output (e.g., the difference between consecutive outputs), the resulting signal is enhanced to show sudden changes in acceleration more clearly. Thus, the signal processing block 202 includes a signal differentiation block 214 that receives the digital filter 212 output and outputs the derivative (i.e., d/dt) of the signal to the decision logic block 204. While in some embodiments this additional signal processing can be optional, enhancing the signal does make the process more robust (e.g., more tolerant of "shake", e.g., from normal jostling) and more reliably able to accurately identify a tap event.

To determine the relative mobility of the devices towards each other (i.e., how quickly the devices are getting closer), the rate of change of the BLE signal strength signal 208 is determined by taking the derivative of the signal 208. Thus, the signal processing block 202 includes a second signal differentiation block 216 that receives the BLE signal strength signal 208 and outputs the derivative (i.e., d/dt) of the signal to the decision logic block 204.

The decision logic block 204 includes a first comparator 218 with inputs coupled to the enhanced signal derived from the high pass digital filter 212 output and a tap threshold value 220 selected to be large enough to insure that the devices were intentionally taped against one another but not so large that the tap could cause damage to either device. The output of the first comparator 218 generates a binary signal that when "TRUE" indicates if the acceleration associated with the tap event was sufficient to exceed the tap threshold value 220.

The decision logic block 204 also includes a second comparator 222 with inputs coupled to the output of the second signal differentiation block 216 and a mobility threshold value 224 selected to be large enough to insure that the devices were intentionally moved together before the tap event. The output of the second comparator 222 generates a binary signal that when "TRUE" indicates if the relative rate of movement of the devices leading up to the tap event was sufficient to exceed the mobility threshold value 224.

The decision logic block 204 also includes a third comparator 226 with inputs coupled to the BLE signal strength signal 208 and a proximity threshold value 228 selected to be large enough to insure that the devices were close enough together at the time of the tap event to insure that they contacted each other. The output of the third comparator 226 generates a binary signal that when "TRUE" indicates that the devices were close enough together (e.g., signal strength indicates proximity) to exceed the proximity threshold value 228.

Coupled to the outputs of the three comparators 218, 222, 226, a logic AND gate 230 receives the binary signals from each. The logic AND gate 230 generates the binary output signal 210 which indicates to pair only if all three binary signals from the three comparators 218, 222, 226 are "TRUE". If any comparator binary output signal is not "TRUE", the logic AND gate 230 generates a signal indicating that the devices should not be paired.

Figure 3:
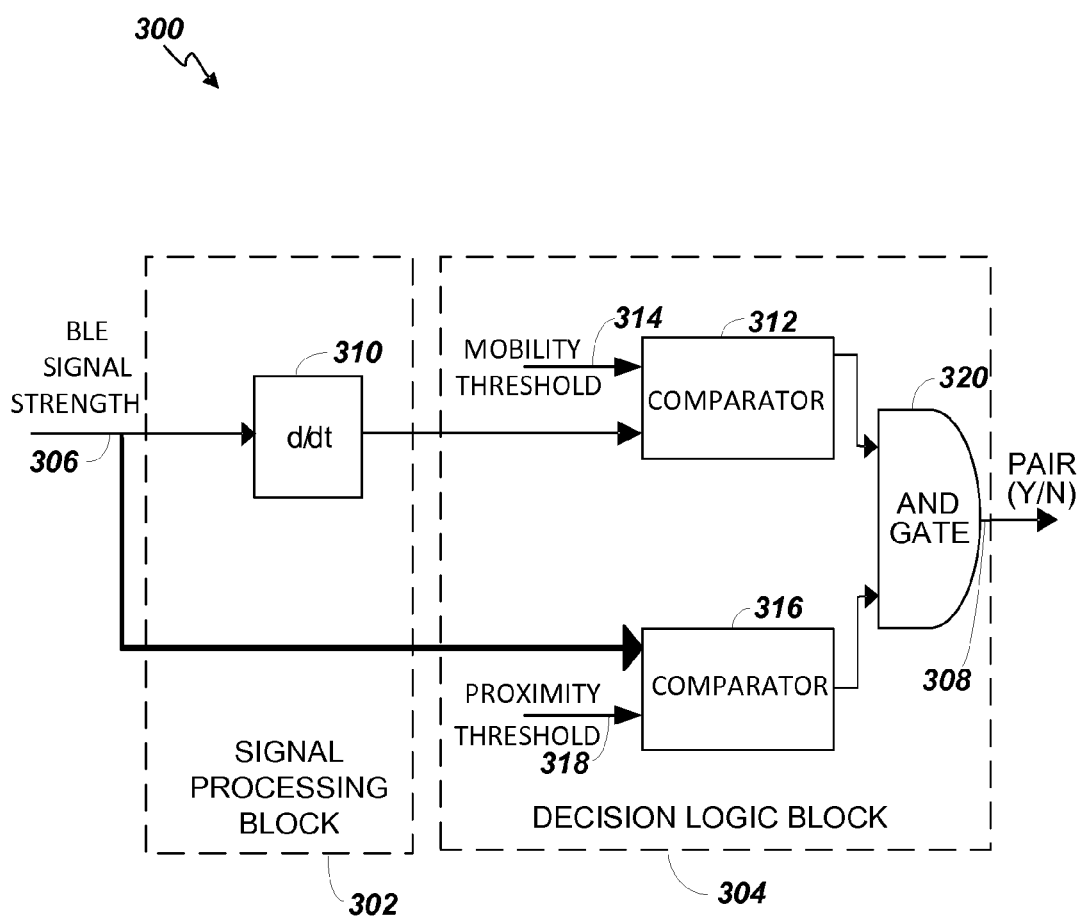
FIG. 3 depicts a logic block diagram of a second example circuit according to embodiments of the present invention.

The above described embodiment uses an accelerometer on the smartphone side to detect a tap event. In embodiments that do not involve a tap event, an accelerometer is not needed. FIG. 3 depicts a logic circuit 300 for a pairing method based on detecting the occurrence of a pre-defined proximity pattern or pairing motion sequence/event instead of a tap event. The pre-defined proximity pattern can be, for example, moving the devices apart to a threshold maximum distance and then moving the devices together to a threshold minimum distance, both movements occurring at a rate above a mobility threshold. Other proximity/motion patterns can be used such as moving the devices together and then apart or moving the devices apart slowly at first and then more rapidly after a certain distance apart is reached.

The logic circuit 300 of FIG. 3 is configured to detect a simple pre-defined proximity pattern or pairing motion sequence/event wherein pairing occurs if the devices start next to each other and are then moved apart at a rate above a mobility threshold. In some embodiments with more complex proximity patterns, the example logic circuit 300 can be used for an initial determination that the devices were moved apart faster than a certain rate and a second logic circuit can be used to determine that a second movement occurred faster than a certain rate. The two movements together can be used to separately satisfy two pairing conditions. Likewise, the logic circuit 300 can be adjusted to detect different pairing motion events at different times to detect a sequence of movements that satisfies corresponding pairing conditions.

The example logic circuit 300 includes a signal processing block 302 and a decision logic block 304. The signal processing block 302 receives a BLE signal strength signal 208 from the BLE radio receiver. Based on this input signal and two threshold values, the logic circuit 300 creates a binary output signal 308 that indicates whether to pair or not.

To determine the relative mobility of the devices towards each other (i.e., how quickly the devices are getting closer), the rate of change of the BLE signal strength signal 306 is determined by taking the derivative of the signal 306. Thus, the signal processing block 302 includes a signal differentiation block 310 that receives the BLE signal strength signal 306 and outputs the derivative (i.e., d/dt) of the signal to the decision logic block 304.

The decision logic block 304 includes a first comparator 312 with inputs coupled to the output of the signal differentiation block 310 and a mobility threshold value 314 selected to be large enough to insure that the devices were moved apart faster than a minimum required rate selected to indicate the movement was intentional. The output of the first comparator 312 generates a binary signal that when "TRUE" indicates if the relative rate of movement apart of the devices was sufficient to exceed the mobility threshold value 314.

The decision logic block 304 also includes a second comparator 316 with inputs coupled to the BLE signal strength signal 306 and a proximity threshold value 318 selected to be large enough to insure that the devices were moved far enough apart to indicate the movement was intentional. The output of the second comparator 316 generates a binary signal that when "TRUE" indicates that the devices were moved far enough apart (e.g., signal strength indicates proximity) to exceed the proximity threshold value 318.

Coupled to the outputs of the two comparators 312, 316, a logic AND gate 320 receives the binary signals from each. The logic AND gate 320 generates the binary output signal 308 which indicates to pair only if both binary signals from the two comparators 312, 316 are "TRUE". If either comparator binary output signal is not "TRUE", the logic AND gate 320 generates a binary output signal 308 indicating that the devices should not be paired.

Figure 4:
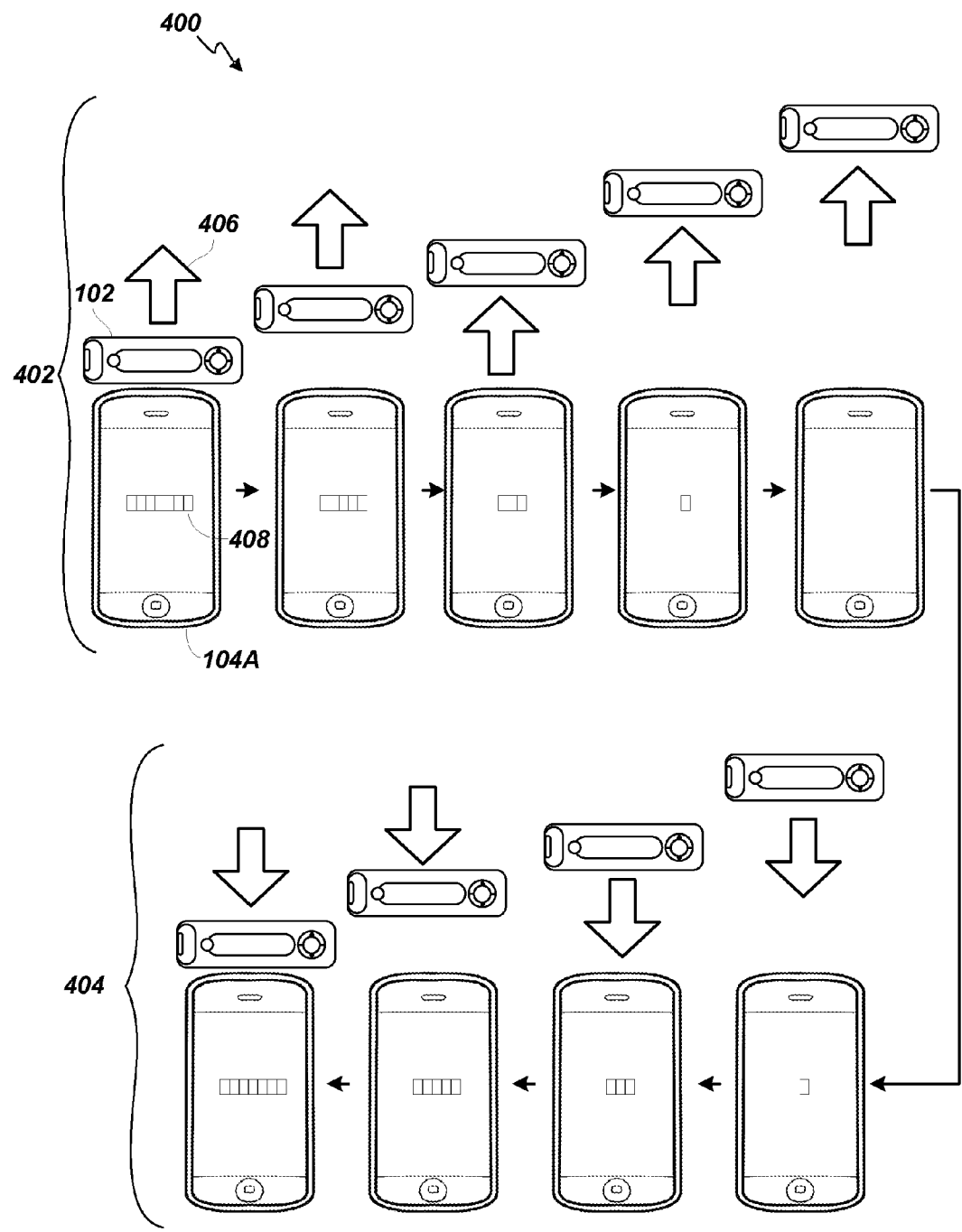
FIG. 4 depicts a pairing motion sequence according to embodiments of the present invention.

Turning now to FIG. 4, an example pairing motion sequence 400 or proximity pattern is illustrated. The pairing motion sequence 400 includes a first motion event 402 where the devices (e.g., a smartphone 104A and a BGM 102), which are initially adjacent each other, are moved apart to at least a pre-defined distance from each other and a second motion event 404 where the devices are moved together. The motion direction arrows 406 (only one labeled) indicated the movement of the BGM 102 away from the smartphone 104A during the first motion event 402 and toward the smartphone 104A during the second motion event 404. Note that the first motion event 402 is broken down into five steps and with each step the BGM 102 is moved a bit further away from the smartphone 104A. Likewise, the second motion event 404 is broken down into four steps and with each step the BGM 102 is moved a bit closer to the smartphone 104A.

Also note that as a reference for a user, an optional segmented proximity indicator bar 408 is displayed on the smartphone 104A. The segmented proximity indicator bar 408 can be part of a user interface adapted to aid a user in executing the pairing motion sequence. The display changes based upon the relative distance between the BGM 102 and the smartphone 104A. The closer the two devices, the more segments of the indicator bar are displayed and the further apart the two devices, the fewer segments of the indicator bar are displayed. Thus, for example, when the user has moved the devices far enough apart to satisfy the pre-defined distance condition of the pairing motion sequence 400, the segmented proximity indicator bar 408 disappears. Likewise, when the pairing motion sequence 400 starts and ends, the segmented proximity indicator bar 408 is displayed with all of the segments.

In some embodiments, alternative displays or graphics can be used to indicate the proximity of the devices to each other. For example, instead of or in addition to a segmented bar, a series of concentric circles can be used. In some embodiments, colors can be used. For example, a color spectrum ranging from red to purple can be used where red indicates the devices are proximate to each other and purple indicates the devices are distant from each other. Further, in some embodiments, sound can be used. For example, a rapid beeping sound, fast tempo music, and/or high pitch tones can indicate the devices are proximate to each other and a slow beeping, slow temp music, and/or low pitch tones can indicate the devices are distant from each other. In some embodiments where the pairing motion sequence requires that the motions be performed at a rate faster than a mobility threshold, graphics, color, and/or sound can be used to indicate that the motions need to be performed faster. For example, if the user is moving the BGM 102 too slowly, the proximity indicator bar 408 can flash red. If the rate exceeds the mobility threshold, the indicator bar can be displayed in a solid blue color.

Figure 5:
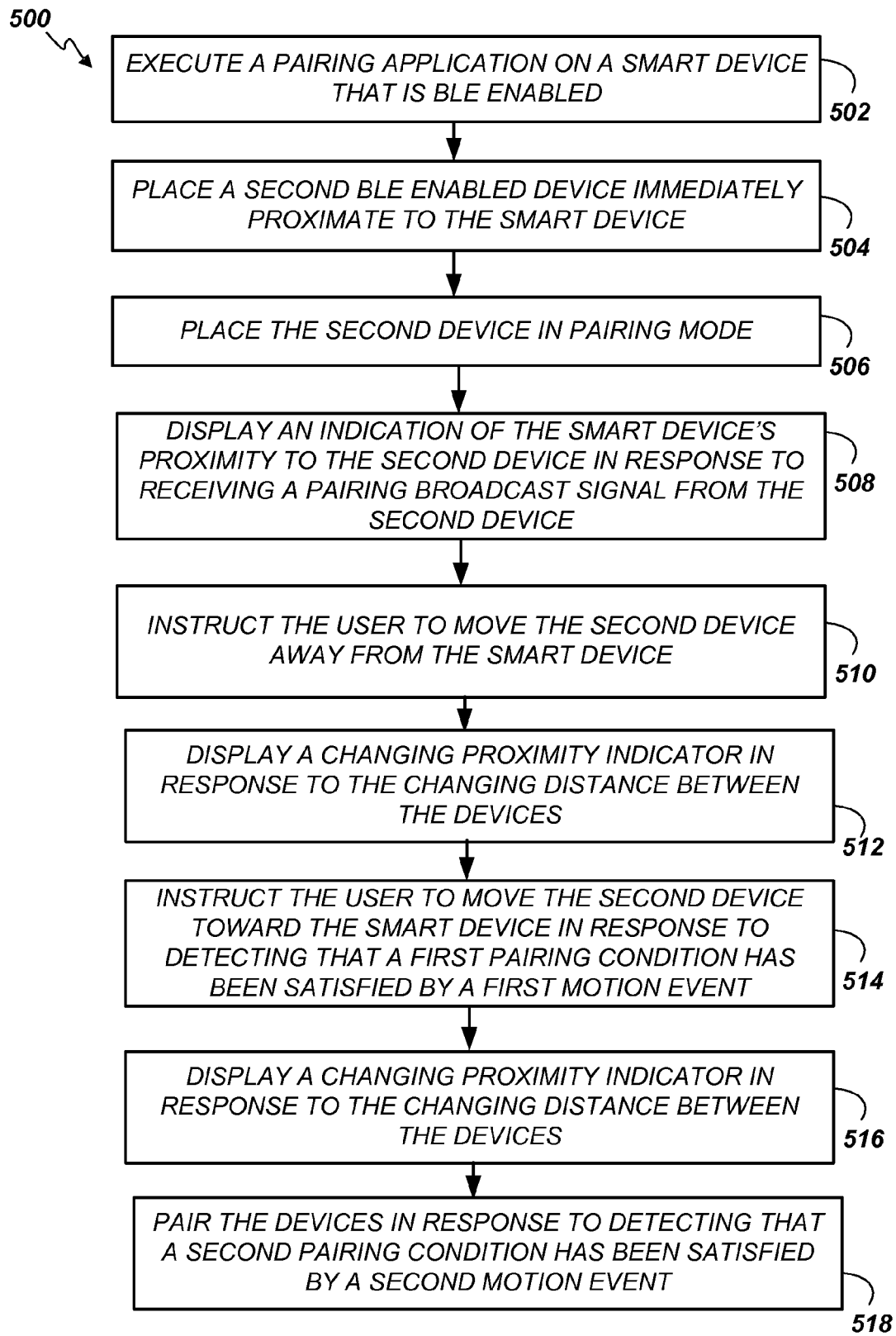
FIG. 5 depicts a flowchart illustrating an example method according to embodiments of the present invention.

Turning now to FIG. 5, a flow chart depicting an example method 500 of pairing wireless devices according to embodiments of the present invention is described. The method 500 starts with executing an application on a smart device (e.g., a smartphone, a tablet, a laptop computer, etc.) that is BLE enabled (502). While embodiments of the invention can use other wireless communication protocols, the example method 500 will be described using BLE to better illustrate the embodiment. The application can be a dedicated pairing application or it can be part of a larger application that will use the wireless connection established by pairing the device. The application can use/implement the embodiments of the logic circuits described above with respect to FIGS. 2 and 3 as well as the user interface embodiments described above with respect to FIG. 4. In some embodiments, the application will place the smart device in a pairing mode.

The second device, which is also BLE enabled, is placed immediately proximate to the smart device (504). The second device is then placed in pairing mode (506). The smart device displays an indication of its proximity to the second device in response to receiving the second device's pairing broadcast signal (508). The smart device instructs the user to move the second device away from the smart device (510). This motion represents a first motion pairing event that once completed, will satisfy a first pairing condition.

In response to the changing distance between the two devices, the smart device displays a changing proximity indicator (512). Once the smart device detects that the second device has been moved away a sufficient distance to satisfy a first predefined pairing motion sequence/event condition, the smart device instructs the user to move the second device toward the smart device (514). This motion represents a second motion pairing event that once completed, will satisfy a second pairing condition.

In response to the changing distance between the two devices, the smart device displays a changing proximity indicator (516). Once the smart device detects that the second device has been moved close enough to the smart device to satisfy a second predefined pairing motion sequence condition, the smart device pairs with the second device (518).

This example includes two pairing conditions that are satisfied at two different times but in a pre-defined sequence. As indicated above, the pairing conditions can require multiple motion events that can be required to be completed in parallel and/or in a sequential order.

The "tap to pair" embodiments described above with respect to FIG. 2 uses an accelerometer on the smart device side to detect a tap event. Other embodiments of the present invention allow the same methods to be used to pair two wireless devices in the case where the smart device has no accelerometer, it is desired to not use the accelerometer, and/or additional security is desired.

Figure 6:
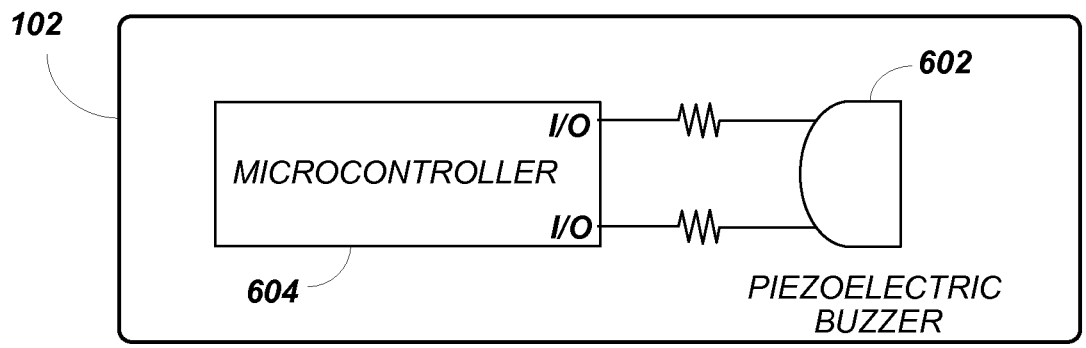
FIG. 6 depicts a block diagram of a blood glucose monitor configurable for use in embodiments of the present invention.
Figure 7:
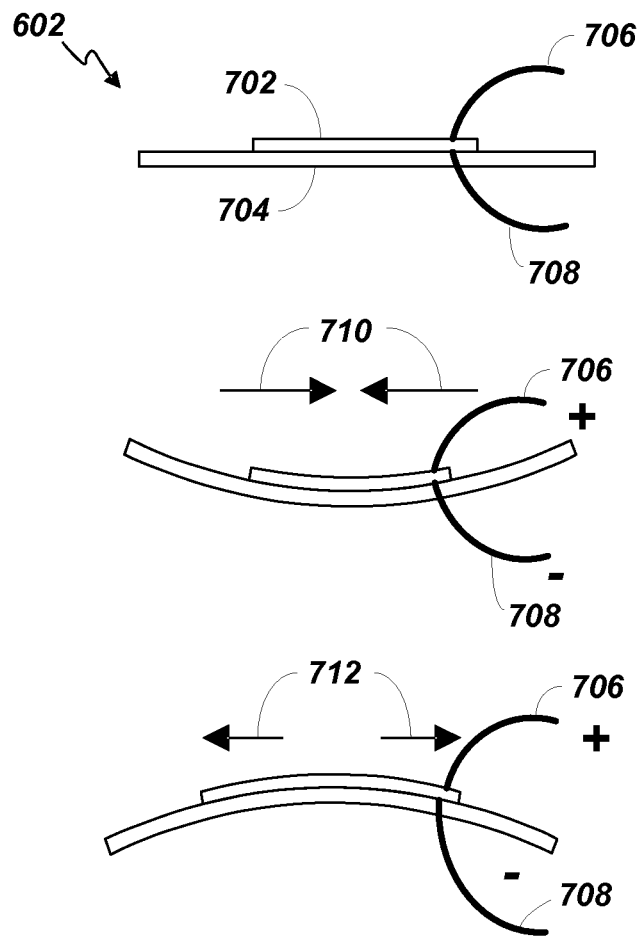
FIG. 7 depicts a side view of a piezoelectric buzzer suitable for use in embodiments of the present invention.

Turning to FIG. 6, many handheld electronic devices, such as BGMs 102, have piezoelectric acoustic components, such as piezoelectric buzzers 602 or speakers, which are driven by microcontrollers 604. As shown in FIG. 7, a piezoelectric acoustic component (e.g., a piezoelectric buzzer 602) includes an active element 702 (e.g., piezoelectric crystal) formed as a plate or disk that is coupled to a mechanical diaphragm 704. An electric audio signal or any alternating current (e.g., from a microcontroller 604) is applied to the active element 702 via a positive electrode 706 and a negative electrode 708 each electrically coupled to opposite surfaces of the active element 702. The active element 702 responds to the electric signal by flexing in proportion to the voltage applied across the active element's surfaces as indicated by arrows 710 and 712. The response thus converts electrical energy into mechanical acoustic energy. The active element 702 includes polarized material (i.e., a material made of molecules that are positively charged on one end and negatively charged on the other). When an electric field is applied across the polarized material, the polarized molecules will align themselves with the electric field, resulting in induced dipoles within the molecular or crystal structure of the material. This alignment of molecules causes the material to change dimensions. This phenomenon is known as electrostriction. In addition, a permanently polarized material such as for example, quartz ($SiO_2$) or barium titanate ($BaTiO_3$), will produce an electric field when the material changes dimensions as a result of an imposed mechanical force. This phenomenon is known as the piezoelectric effect. Therefore, the same piezoelectric buzzer 602 can work as both a sound transducer as well as a signal generating vibration/impact sensor.

Embodiments of the present invention use a wireless device's existing piezoelectric buzzer 602 to generate an interrupt for the microcontroller 604 when the device is tapped (e.g., the mechanical diaphragm 704 vibrates in response to the device being tapped and the active element 702 generates an electrical signal in response to being compressed by the vibrating diaphragm 704). This signal response to a tap can be used in the pairing process between the two devices. From the perspective of a wireless device manufacturer that wants to create devices that can pair with any smart device, using the peripheral or secondary device's piezoelectric acoustic component instead of the smart device's accelerometer can be beneficial since the pairing does not depend on correctly determining accelerometer sensitivity (e.g., different smart devices may have different sensitivities), since the sensitivity of the second device (e.g., a BGM 102) is predictable and controllable. Another benefit of this approach is that almost all the electronic hardware needed is typically present or available, so that no additional external integrated circuits are required.

Figure 8:
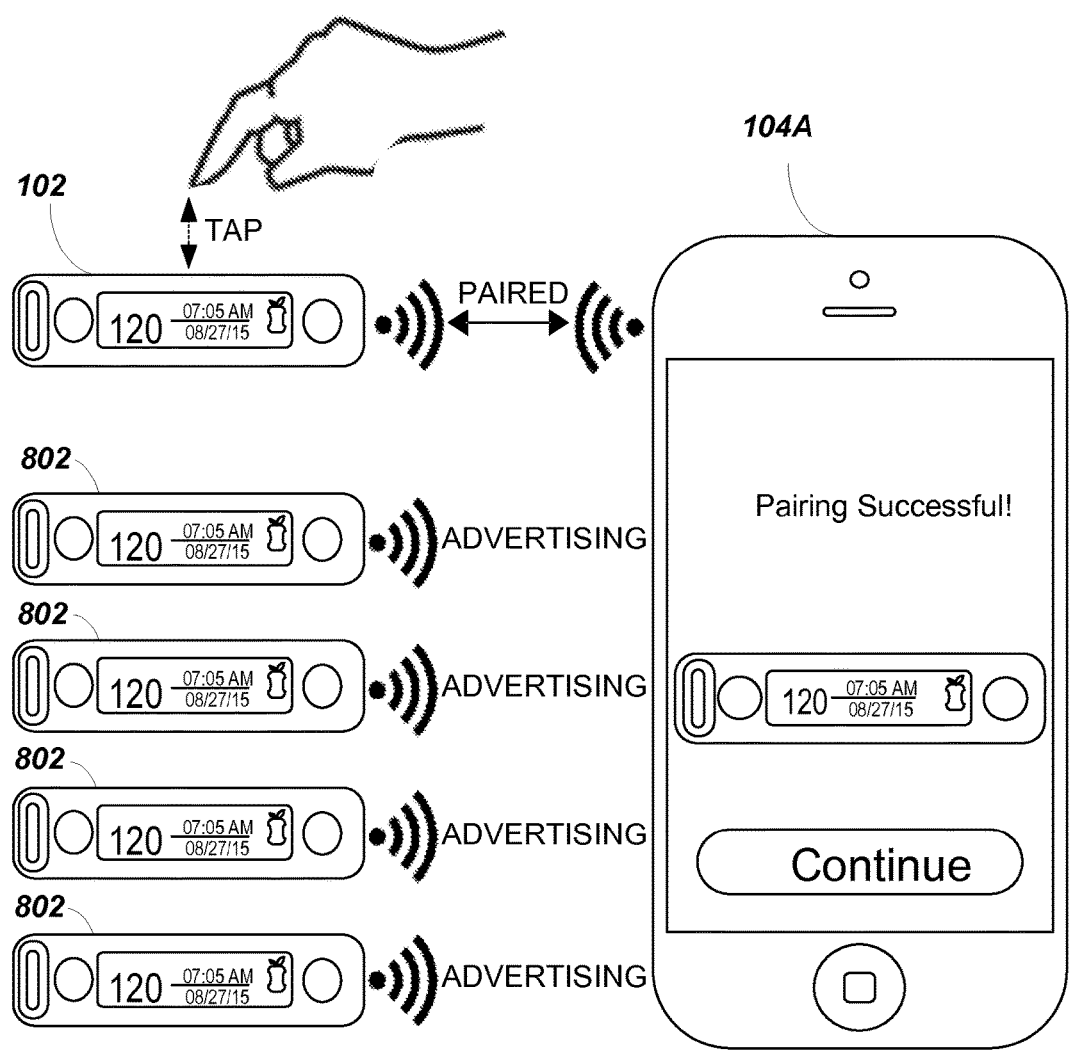
FIG. 8 depicts an example system diagram illustrating an example pairing method according to embodiments of the present invention.

FIG. 8 depicts an example pairing method according to embodiments of the present invention. Assume that a smartphone 104A and a BGM 102 with a piezoelectric buzzer 602 are ready for pairing. Further assume that there are several "eavesdropping" BGMs 802 within pairing range of the smartphone 104A that are also in pairing mode and continuously advertising for a connection. When the BGM 102 is put in pairing mode and thus advertising, if it is tapped, the BGM 102 senses the tap event using the piezoelectric buzzer 602 and transmits this information to the smartphone 104A. In response, the smartphone 104A then pairs with the BGM 102 that was tapped.

In alternative embodiments, a pairing condition can be that both the BGM 102 and the smart phone 104A are required to detect a tap event that occurs at the same time (e.g., within a very small window to account for signal lag etc.). For example, the smartphone 104A and the BGM 102 can be tapped against each other and each individually detects the tap event, the BGM 102 using its piezoelectric buzzer 602 and the smartphone 104A using its accelerometer and/or its own piezoelectric speaker. The BGM 102 can transmit a report of the tap event to the smartphone 104A along with both a "current" timestamp and a timestamp for the tap event. The smartphone 104A can use the information and its own record of the tap event to determine if the tap event that the BGM 102 reported happened at the same time (e.g., within a very small window to account for signal lag etc.) as the tap event that the smartphone 104A recorded. (Note that the smartphone 104A can use the "current" timestamp from the BGM 102 to synchronize its own clock with the BGMs to compare the tap event timestamps.) Along with proximity and mobility information described above with respect to embodiments depicted in FIGS. 2 and 3, the smartphone 104A can determine with a high degree of certainty if the BGM 102 was tapped against the smartphone 104A and thus, is the correct device with which to pair.

Figure 9:
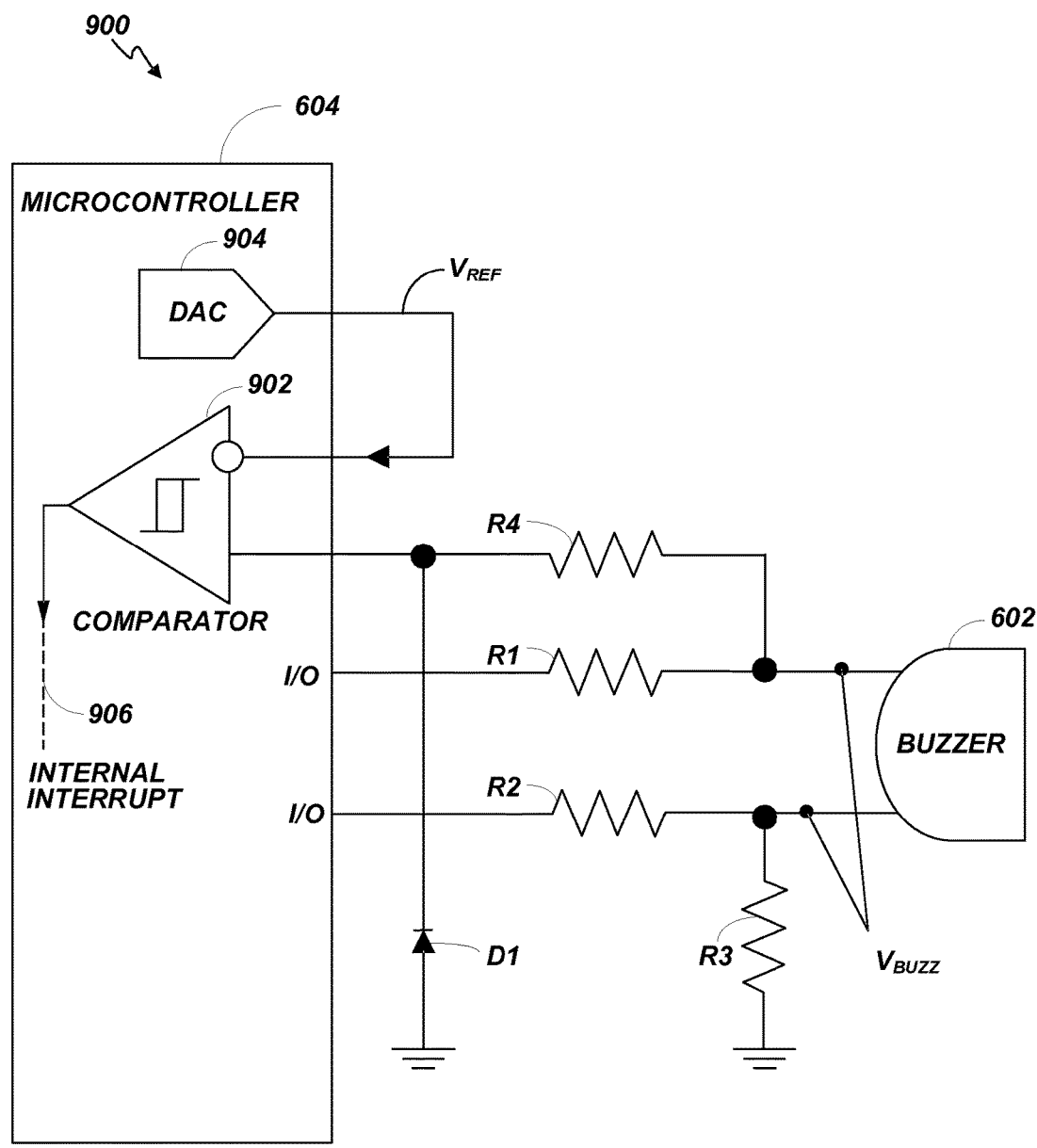
FIG. 9 is a block diagram depicting an example dual use piezo circuit according to embodiments of the present invention.
Figure 10:
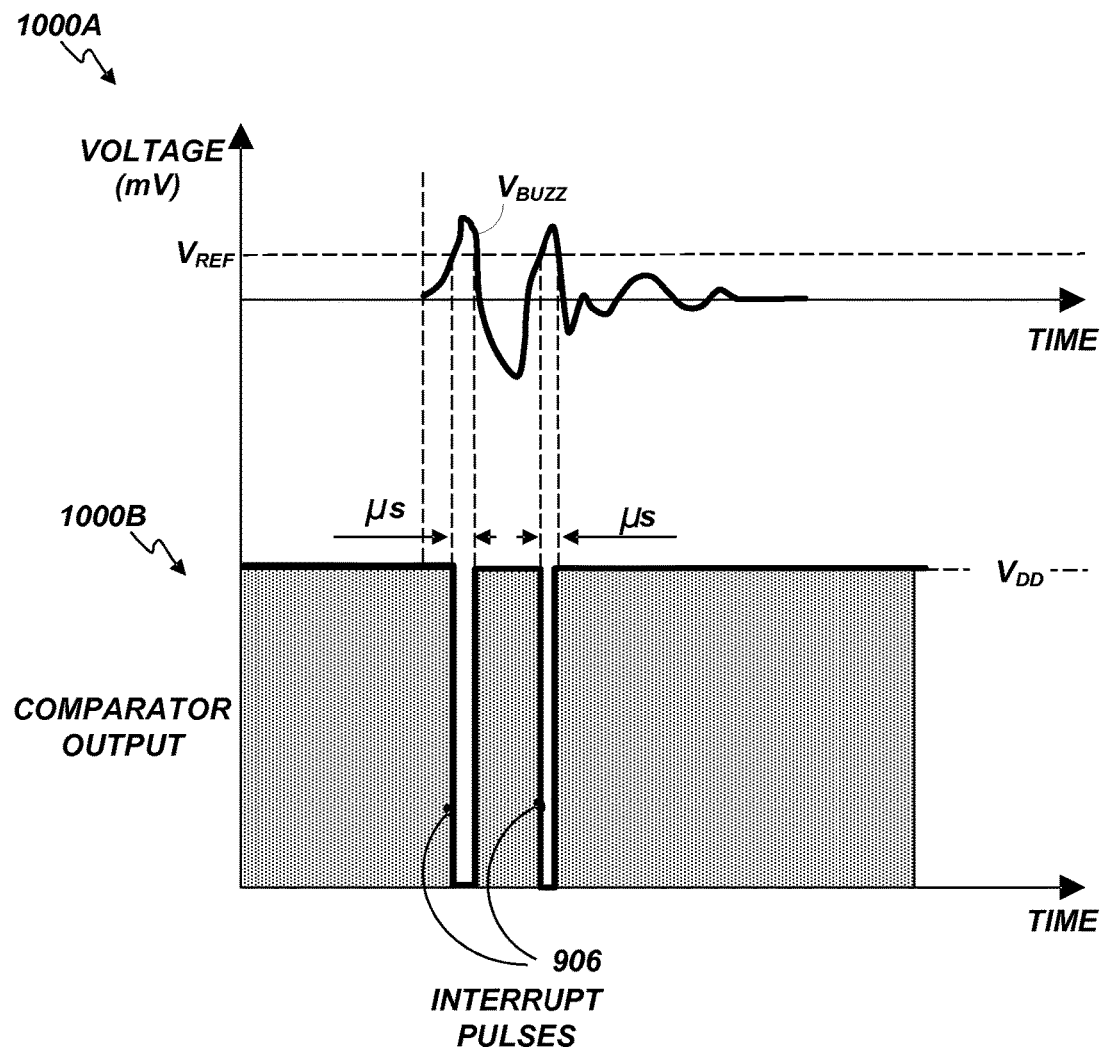
FIG. 10 is a graph of example signals generated by the dual use piezo circuit of FIG. 9.

FIG. 9 depicts an example dual use piezo circuit 900 that allows a piezoelectric acoustic component (e.g., a piezoelectric buzzer 602) to function as both a sound generator and a vibration/impact sensor according to embodiments of the present invention. The circuit 900 facilitates concurrently connecting the buzzer 602 for performing both functions even though the functions are not executed concurrently. The piezoelectric buzzer 602 is driven by two I/O pins from the microcontroller 604. Since the piezoelectric buzzer 602 is not used to generate sound while pairing, which is the time period during which embodiments of the present invention use the piezoelectric buzzer 602 for "tap detection", there is no concern regarding race conditions in the dual use configuration depicted in FIG. 9. When the wireless device is tapped, the piezoelectric buzzer 602 generates a low amplitude electrical signal $V_{BUZZ}$ as depicted in the top graph 1000A of FIG. 10. The frequency of this signal is close to the piezoelectric buzzer's resonant frequency and its amplitude is on the order of millivolts. This signal is a function of the mechanical design and specific piezoelectric buzzer characteristics. The amplitude of this signal is not sufficient to generate an interrupt at the microcontroller 604. However, using a comparator 902, the low amplitude signal can be detected and a microcontroller interrupt can be generated in response. Many mixed-signal microcontrollers have embedded analog-to-digital converters (ADCs), digital-to-analog converters (DACs), and analog comparators which can be utilized to implement this example embodiment of the present invention.

For example, an embedded DAC 904 within the microcontroller 604 can be programmed to generate a DC reference voltage $V_{REF}$ to serve as the threshold voltage for a comparator 902. The comparator 902 compares the signal $V_{BUZZ}$ from the piezoelectric buzzer 602 with the reference voltage $V_{REF}$. If the signal level exceeds the threshold (i.e., $V_{BUZZ} > V_{REF}$), the comparator 902 generates an interrupt pulse (or pulses) as shown in the lower graph 1000B of FIG. 10. The output of the comparator 902 has a normal digital voltage level $V_{DD}$ that can be detected by the microcontroller 604 and used as an interrupt. The diode D1 eliminates the negative component of the bipolar piezoelectric buzzer signal $V_{BUZZ}$. Some piezoelectric buzzers 602 with high resonant frequency may generate very short input pulses (e.g., on the order of microseconds) that are not long enough to be processed by the microcontroller 604. The speed of interrupt processing depends on the specific microcontroller 604, clock frequency and interrupt handler design.

Figure 11:
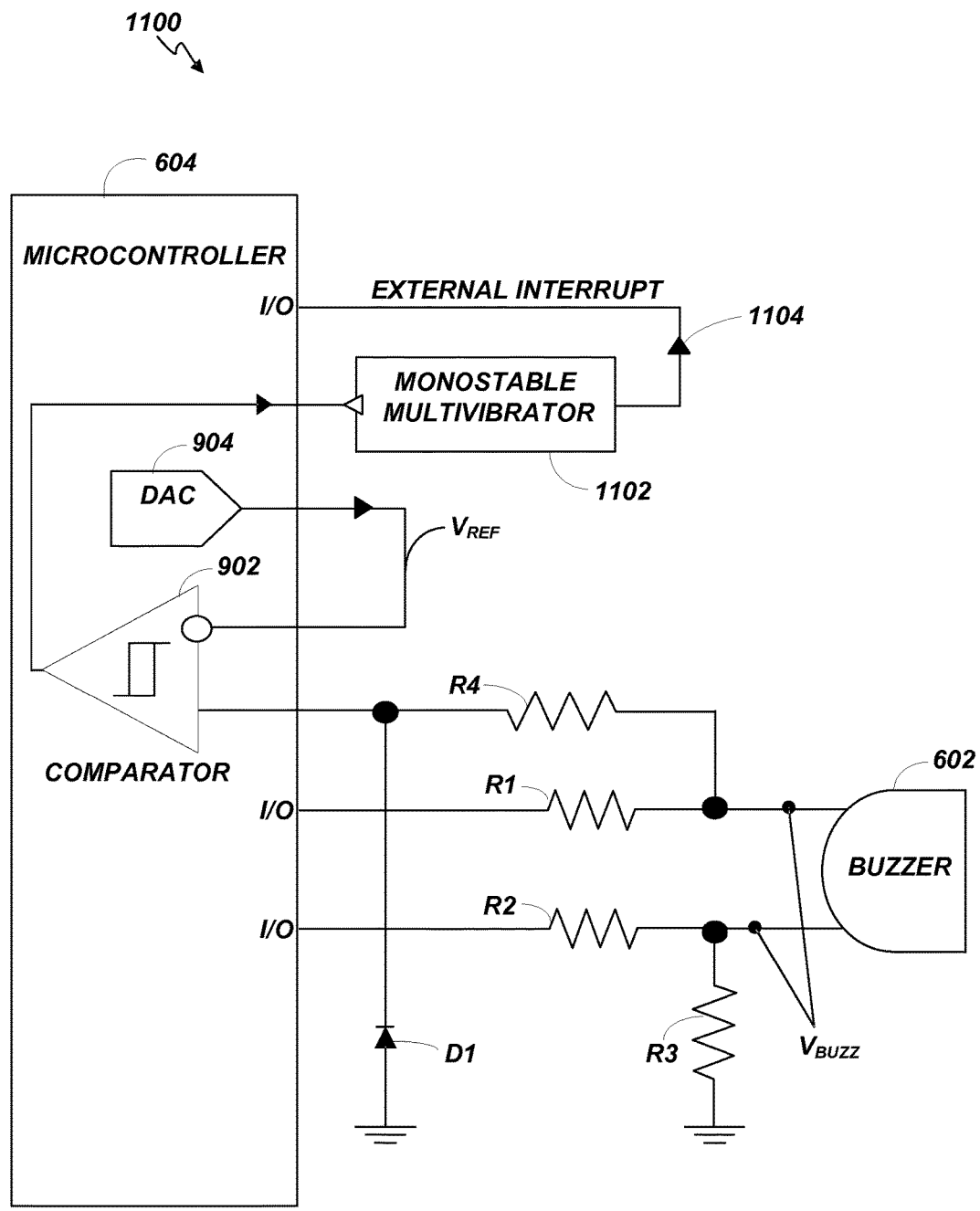
FIG. 11 is a block diagram depicting an example dual use piezo circuit according to embodiments of the present invention.
Figure 12:
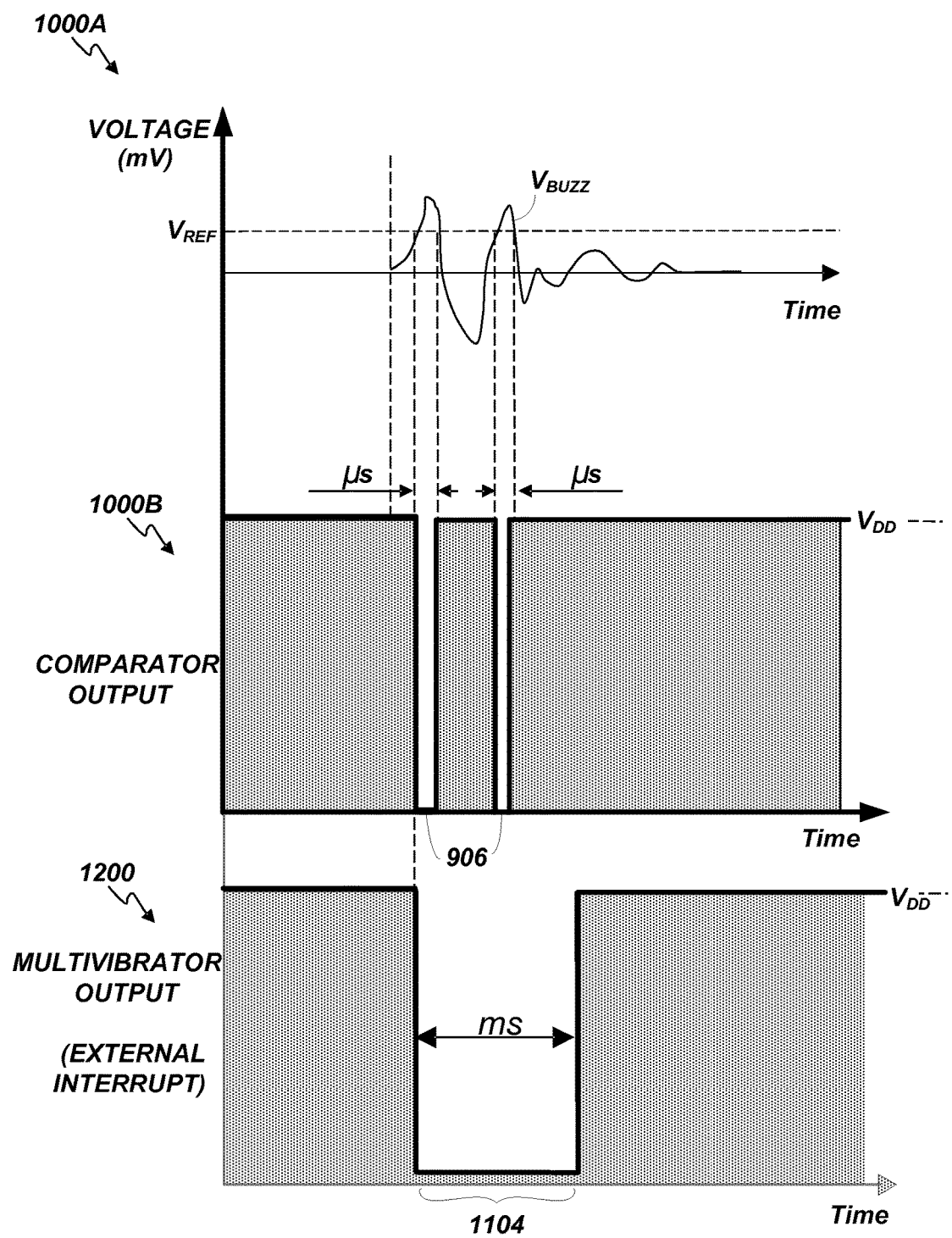
FIG. 12 is a graph of example signals generated by the dual use piezo circuit of FIG. 11.

In an alternative embodiment, a monostable multivibrator 1102 can be used as shown in the alternative dual use piezo circuit 1100 of FIG. 11. The multivibrator 1102 receives a short input pulse 906 from the comparator 902 and generates a stable output pulse 1104 with any configurable duration as shown in graph 1200 of FIG. 12. This output pulse does not depend on the duration of the short input pulse 906. The output pulse duration can be adjusted so that even a slow speed microcontroller 604 can process the generated interrupt. The interrupt duration is stable and absolutely predictable, which simplifies interrupt processing.

Figure 13:
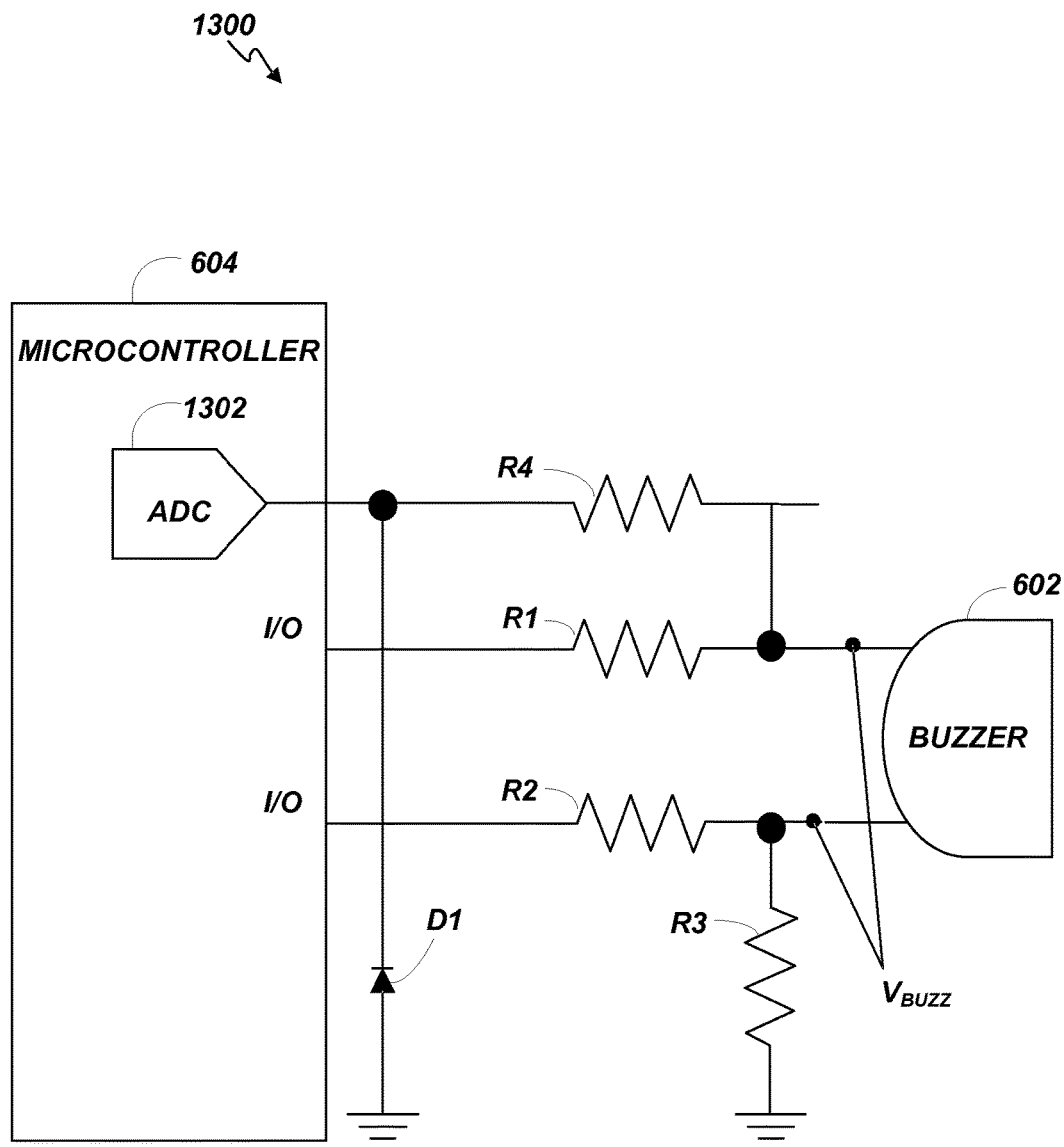
FIG. 13 is a block diagram depicting an example dual use piezo circuit according to embodiments of the present invention.

As mentioned above, many microcontrollers have embedded ADCs. As shown in FIG. 13, another alternative dual use piezo circuit 1300 can use an ADC 1302 to detect a tap event in the signal $V_{BUZZ}$ generated by the piezoelectric buzzer 602. Unlike the methods described above, the signal $V_{BUZZ}$ generated by the piezoelectric buzzer 602 is not used to generate an interrupt. When the peripheral device (e.g., BGM 102) is attempting to pair, the microcontroller 604 enables ADC measurement. The ADC 1302 continuously poles the input voltage $V_{BUZZ}$. When the peripheral device (e.g., BGM 102) is tapped, the ADC 1302 receives the $V_{BUZZ}$ signal from the piezoelectric buzzer 602 and converts it into a digital value. If this value exceeds a pre-defined "tap" threshold (e.g., determined based on a calibration procedure), the microcontroller 604 in the peripheral device generates a signal indicating the tap event occurred. The signal is incorporated into the advertising data (as in the previous methods). A smart Device (e.g., a smartphone 104A) completes pairing upon receiving this data. Thus, only the peripheral device that generates a signal when tapped will connect to the smart device. All other advertising peripheral devices are ignored. This embodiment using an ADC 1302 also allows the implementation of a digital filter to reduce electrical noise.

Beyond pairing, there are numerous additional applications for the dual use piezo circuits of the embodiments of the present invention. For example, in electronic devices warrantied against manufacturing defects but not against impacts, a dual use piezo circuit can be used to record (e.g., with a timestamp) whether the device has undergone a significant impact. The recording can be used forensically to resolve responsibility for a warranty claim.

In another application, the dual use piezo circuit can be used in conjunction with a security function. For example, similar to a password protection system, the device can be intentionally disabled until a user selected rhythm pattern of taps is detected by the dual use piezo circuit. This use could provide password protection in the form of a rhythm pattern for a device that does not have a facility for entering alpha-numeric characters (e.g., a keyboard).

In yet another application, the dual use piezo circuit can be used as a trigger for setting of an alarm if the electronic device is touched or moved by an unauthorized person. For example, an audio alarm can be set to sound if is moved without disabling the alarm within a short time frame (e.g., by pressing a button sequence or tapping a rhythm on the device).

Figure 14:
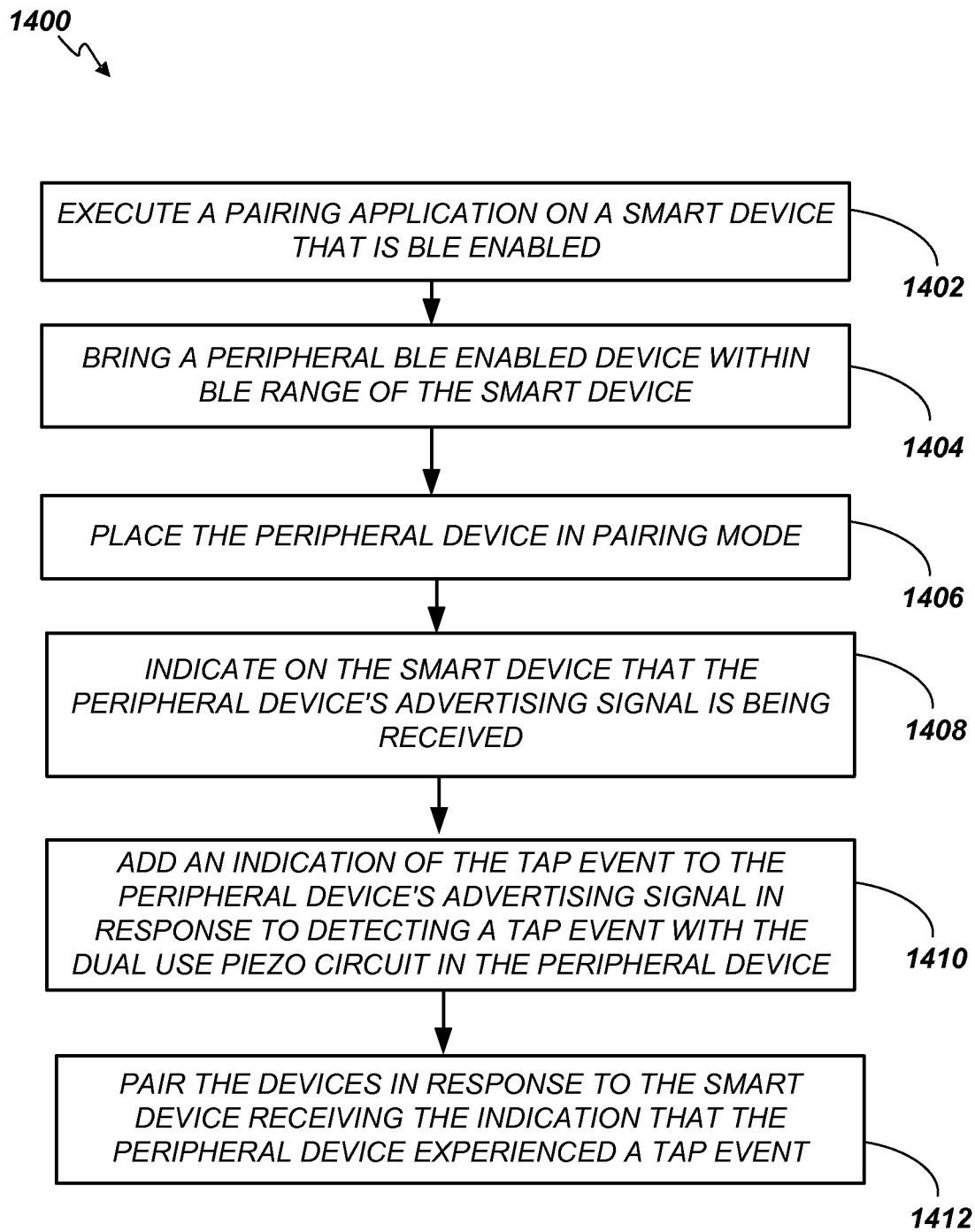
FIG. 14 depicts a flowchart illustrating an example method according to embodiments of the present invention.

Turning now to FIG. 14, a flow chart depicting an example method 1400 of pairing with a dual use piezo circuit is shown. The method 1400 starts with executing an application on a smart device (e.g., a smartphone, a tablet, a laptop computer, etc.) that is BLE enabled (1402). While embodiments of the invention can use other wireless communication protocols, the example method 1400 will be described using BLE to better illustrate the embodiment. The application can be a dedicated pairing application or it can be part of a larger application that will use the wireless connection established by pairing the device. The application can use/implement the embodiments of the circuits described above with respect to FIGS. 2, 3, 9, 11, and 13 as well as the user interface embodiments described above with respect to FIG. 4. In some embodiments, the application will place the smart device in a pairing mode.

The peripheral device, which is also BLE enabled, is brought within BLE range of the smart device (1404). The peripheral device is then placed in pairing mode (1406). The smart device displays an indication of receiving the peripheral device's advertising signal (1408). In response to detecting a tap event with a dual use piezo circuit of embodiments of the present invention, the peripheral device adds information indicating the occurrence of the tap event to the advertising broadcast (1410). The tap represents a first motion pairing event that once the smart device receives notice, will satisfy a first pairing condition. In response to receiving the indication that the peripheral device experienced a tap event, the smart device pairs with the peripheral device (1412). In some embodiments, the smart device can require satisfaction of additional pairing conditions such as, for example, meeting a proximity threshold and/or a mobility threshold.

Figure 15:
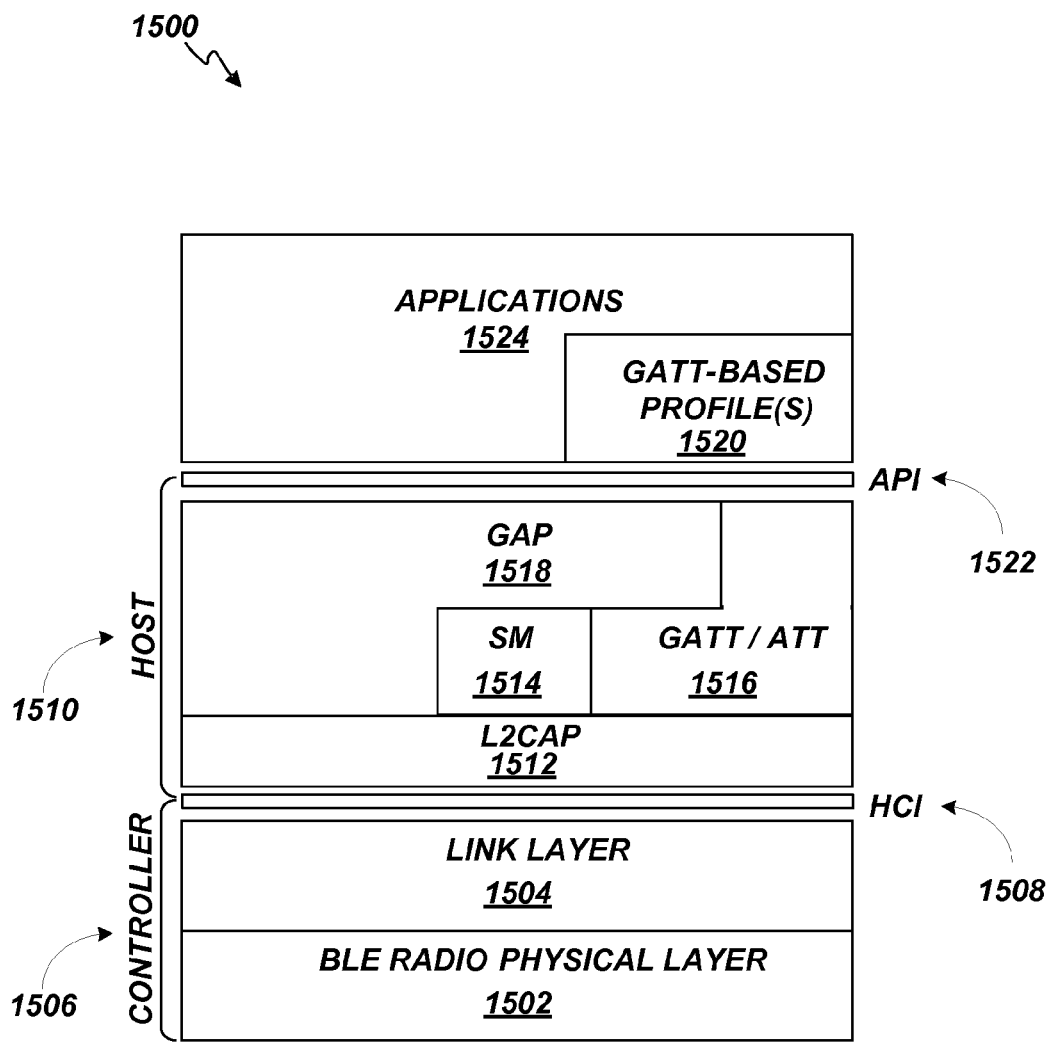
FIG. 15 is a block diagram depicting a simplified structure of the BLE protocol stack.

Turning now to FIG. 15, a simplified depiction of a BLE protocol stack 1500 is provided to illustrate embodiments of the present invention that can use the BLE advertising broadcast transmission, e.g., to minimize pairing to only when new data is available for transfer. BLE Radio implementation supports the physical layer 1502 of the protocol stack 1500 while the link layer 1504 controller is responsible for low level communication over a physical layer 1502 interface. The link layer 1504 manages the sequence and timing of transmitted and received frames, and it handles a state machine for advertising, scanning and the connection state. Collectively, this lower part of the BLE protocol stack 1500 (i.e., the physical layer 1502 and the link layer 1504) is called the controller 1506 and is tightly integrated with the BLE radio. The controller 1506 runs lower layers of the stack which handle physical layer packets and all associated timing.

The upper part of the BLE protocol stack 1500 has much more relaxed timing constraints and may be implemented on the same microcontroller or use a separate hosting microcontroller. Communication between the BLE controller and host is standardized using the Hardware Controller Interface 1508 (HCI) which allows complete decoupling of the BLE controller from the Host 1510 part of the protocol stack 1500.

The Logical Link Control and Adaptation layer Protocol 1512 (L2CAP) component is a multiplexor responsible for aggregation and directing data streams between the BLE controller and different components in the Host 1510 part of the protocol stack 1500: Security Manger 1514 (SM), the generic attribute profile 1516 (GATT) and generic access profile 1518 (GAP). The Security Manger 1514 provides a mechanism to encrypt and authenticate data and is responsible for device pairing and key distribution. The generic attribute profile 1516 describes a service framework used for discovering services, reading and writing characteristic values on a peer device using the attribute protocol (ATT) optimized for small packet sizes used in BLE. GATT-based profiles 1520 (via an application programming interface 1522 (API)) used in BLE minimize the size of the data exchange between the devices and therefore reduces the time the device is in active RF mode. The generic access profile 1518 provides an interface for the applications 1524 to configure and enables different modes of operation, e.g. advertising or scanning, and also to initiate, establish, and manage the connection with other devices.

Combined, all components together of the BLE host 1510 part of the protocol stack 1500 fits into approximately on average 32K of memory depending on supported optional functionality. The BLE protocol stack 1500 is considerably smaller than the memory requirements for regular Bluetooth devices, but it still requires the Host device to have more than just a few K of flash memory for the BLE protocol stack 1500 alone.

Figure 16:
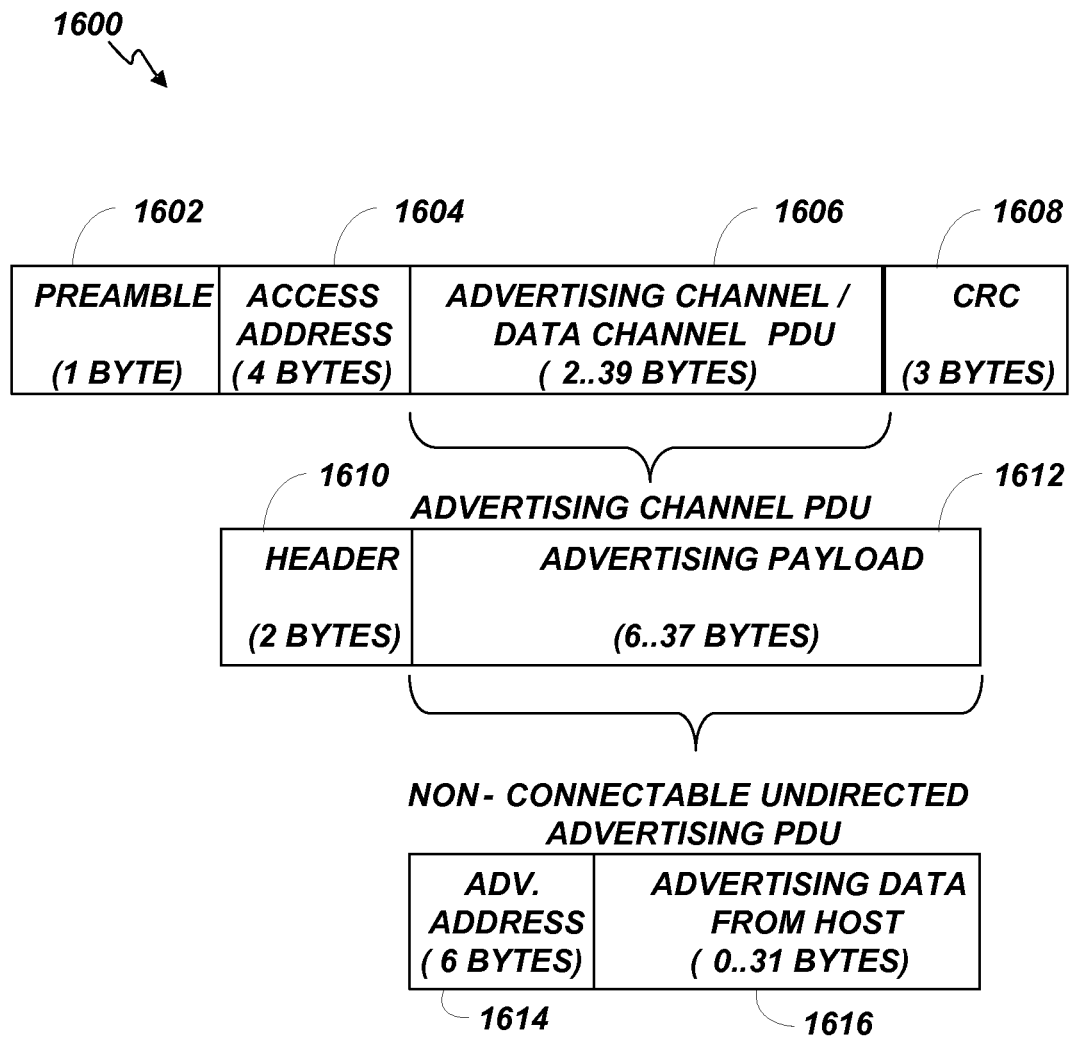
FIG. 16 is a drawing depicting a BLE "over the air" message packet structure.

When the advertising mode is enabled, the BLE device will start to transmit special data packets carrying advertising information as Payload Data Units (PDU) on the RF channels dedicated for this purpose. BLE uses a common structure for over the air packets for both advertising and data channels. Turning now to FIG. 16, an example of a BLE over the air data packet 1600 is depicted. The advertising channel carries the device's discovery and connection establishment information; a non-connectable undirected advertising PDU contains device MAC address and up to 31 bytes of data formatted as advertising data (AD) structures. As shown in FIG. 16, a BLE over the air data packet 1600 includes a preamble 1602 (1 byte), an access address 1604 (4 bytes), a Payload Data Unit 1606 (PDU) (up to 39 bytes) and a CRC 1608 (3 bytes). For data channels, the access address 1604 is different for each link layer 1504 (FIG. 15) connection between two devices, but for advertising channels it has the same 32-bit value (0x8E89BED6).

An advertising channel Payload Data Unit 1606 has a header 1610 (2 bytes) and actual payload 1612 (6 to 37 bytes). The header 1610 contains information about the size of the payload 1612 and its type: advertising channels are used for exchanging information before making a connection (i.e., before pairing) between devices. Hence, different payload types are supported to broadcast information about the device's ability (on inability) to support a connection, to request more information or to respond with additional device information and to request the initiation of a data connection with another device. For example, an information only (e.g., non-connectable) undirected type of payload 1612 that could be used in some embodiments of the present invention includes a media access control (MAC) address 1614 (6 bytes using IEEE format) of the device sending the information and actual information (e.g., AD 1616) up to 31 bytes.

The BLE channel plan includes of 37 data communication channels and three dedicated advertising channels used for device discovery, connection initiation and broadcast. Advertising channels are allocated in different parts of the spectrum to provide immunity against interference from 802.11/Wi-Fi. An advertising event includes sending advertising data on each enabled advertising RF channel (1 to 3 channels can be selected in different embodiments). The time between two consecutive advertising events is defined as an advertising interval and can be configured from 100 ms to 10.24 sec (e.g., the value is a multiple of 0.625 ms) for a non-connectable undirected advertising type. In order to minimize advertising package collision from multiple collocated devices, a random delay interval (0 to 10 ms) is added before each advertising event.

In some embodiments of the present invention, methods and apparatus are provided for securely determining if a wireless device has data to transmit to a receiving device that is new to the receiving device before requesting the transmitting device expend the energy to establish a data connection between the two devices. The embodiments thus preserve battery life by minimizing the frequency of connections. For example, in a BLE embodiment, a Payload Data Unit 1606 can be used by an application 1524 to transmit a state variable value in the wireless device's BLE AD 1616 and the receiving device stores the state variable value. If the value is not the same as a previously stored value, the receiving device assumes that there is new data available and proceeds with pairing to allow transfer of the new data. If the value is the same as the previous value, this indicates that no new data is available and the system saves energy by avoiding unnecessarily pairing the devices.

By using a state variable value instead of an actual or literal indication that the status of the transmitting device has changed, the system can protect confidential information from being transmitted to eavesdropping devices and thereby preserve both the security of the pairing process and a user's confidential information. For example, a user's BGM can be configured as a BLE server that advertises the status of the meter through wireless broadcasts. The status of the meter may include confidential user or patient related information. Since the data broadcasted is not encrypted or can be in an easily decoded format, it is possible that the patient's information will be exposed to an unknown, eavesdropping third party. Thus, by using a state variable value, the BGM does not broadcast the meter status. An example of possible confidential/private data can include the fact that the user has recently completed a blood glucose test and a new result is available on the meter for an application on the user's smart phone to download.

In some embodiments, any user action that leads to a permanent data change on the BGM (e.g., data stored in the non-volatile memory has been modified) can be a basis to change the state variable. Based on the broadcast advertising data alone, a paired or unpaired smart device can determine whether the BGM has new data for it to read from the BGM without connecting to the BGM, thus unnecessary connections to the BGM are avoided.

In some embodiments, an 8-bit state variable can be used as part of advertising data packet. Other size variables, e.g., 16-bit, 32-bit, 64-bit, can be used. The state variable can, for example, be incremented by one, or randomly changed, or decremented by a fixed value every time the values stored in the device's memory (e.g., an EEPROM used as non-volatile memory for user data storage on the BGM or other types of memory) changes. In alternative embodiments a date/time stamp of the data can be used or a data size can be used. More generally, a data characteristic such as a state variable, a date/time stamp, a data size, etc. can be used as the advertising data to indicate that new data is available for transfer.

When there are multiple smart devices are paired with the BGM, the applications running on the smart devices each maintain a last connection status or data characteristic variable of the same size or value. If the status variable is not equal to the state/data characteristic variable received from the advertising data from the meter, the application knows something in the meter has changed. The application can make a connection to the BGM, read the changed data from the BGM, update its own state variable to the same value as broadcast by the BGM, and then disconnect.

Figure 17:
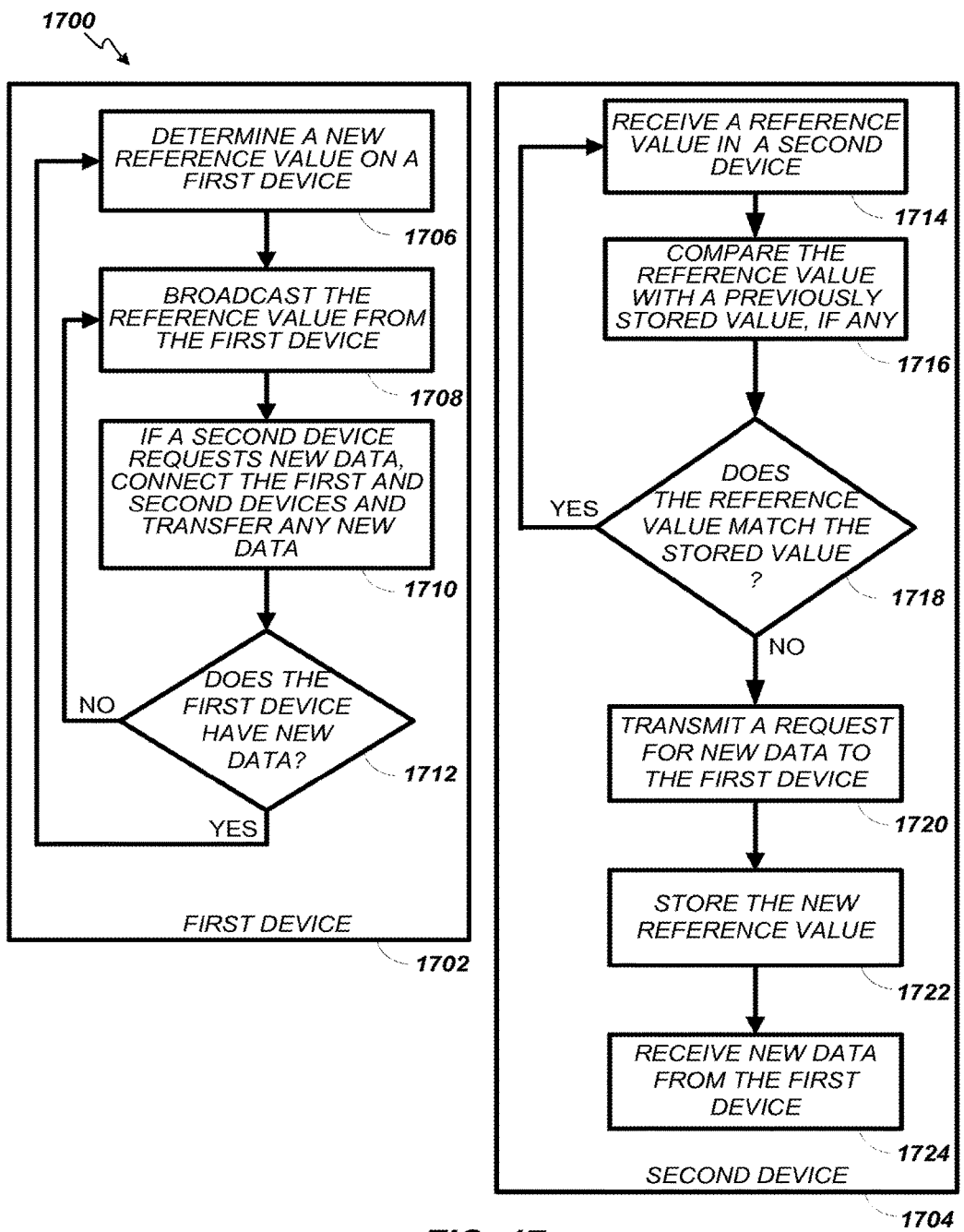
FIG. 17 is a flowchart illustrating an example method according to embodiments of the present invention.

Turning now to FIG. 17, a flow chart depicting an example method 1700 according to embodiments of the present invention is provided. The example method 1700 can be embodied as two related, cooperating processes, one embodied on a first device 1702 (e.g., a BGM with BLE) and one embodied on a second device 1704 (e.g., a smart device such as a smartphone with BLE). Note that other devices enabled with different wireless communication protocols can be used.

On the first device 1702, a reference value is determined (1706). The reference value can be a state variable value, a random value, a time/date stamp, an incremental value, a data characteristic value, a value calculated based upon data stored in the first device's memory, etc. Any practicable method for determining reference values can be used, as long as a different value can be determined when new data is available to be transmitted to the second device 1704. The reference value is then broadcast, for example, in the advertising data by the first device (1708). If a request for new data has been received from the second device 1704, the two devices connect (e.g., establish a wireless communication channel) and the new data is transferred from the first device 1702 to the second device 1704 (1710). Next, it is determined if the first device has new data (1712). For example, if the first device is a sensor or a BGM and a new measurement has been taken since the last measurement, the first device will have new data. In some embodiments, the memory used to store the measurement data can be monitored for any changes to determine if there is new data. If there is new data, then flow returns to determining a new reference value (1706) and the process repeats from there. If there is no new data, flow returns to broadcasting the existing reference value (1708) and the process repeats from there.

Concurrently with the above-described process running on the first device 1702, a second cooperative process runs on the second device 1704. A reference value is received on the second device 1704 from a broadcast of the first device 1702 (1714). The received reference value is next compared with a previously stored reference value (1716). If the values match, it is assumed no new data is available (1718) and flow returns to receiving a reference value (1714). If the values do not match, it is assumed new data is available (1718) and flow proceeds to transmitting a request for new data from the first device 1702 (1720). The new "non-matching" reference value is stored (1722) and the new data from the first device 1702 is received in the second device 1704 (1724) and the process repeats.

In some embodiments, a counter (e.g., an incrementally increasing value) is used as the state variable, in some other embodiments, a random number is used, and in yet still other embodiments, a data characteristic related to the new data is used as the state variable. As long as the state variable value in the BLE advertising data broadcast changes to a value different than the previous value whenever new data is available, any of the above alternatives can be used.

Numerous embodiments are described in this disclosure, and are presented for illustrative purposes only. The described embodiments are not, and are not intended to be, limiting in any sense. The presently disclosed inventive concepts are widely applicable to numerous embodiments, as is readily apparent from the disclosure. One of ordinary skill in the art will recognize that the disclosed embodiments may be practiced with various modifications and alterations, such as structural, logical, software, and electrical modifications. Although particular features of the disclosed invention(s) may be described with reference to one or more particular embodiments and/or drawings, it should be understood that such features are not limited to usage in the one or more particular embodiments or drawings with reference to which they are described, unless expressly specified otherwise.

The present disclosure is neither a literal description of all embodiments nor a listing of features of the invention that must be present in all embodiments.

The Title (set forth at the beginning of the first page of this disclosure) is not to be taken as limiting in any way as the scope of the disclosed invention(s).

The term "product" means any machine, manufacture and/or composition of matter as contemplated by 35 U.S.C. § 101, unless expressly specified otherwise.

The terms "an embodiment", "embodiment", "embodiments", "the embodiment", "the embodiments", "one or more embodiments", "some embodiments", "one embodiment" and the like mean "one or more (but not all) disclosed embodiments", unless expressly specified otherwise.

The terms "the invention" and "the present invention" and the like mean "one or more embodiments of the present invention."

A reference to "another embodiment" in describing an embodiment does not imply that the referenced embodiment is mutually exclusive with another embodiment (e.g., an embodiment described before the referenced embodiment), unless expressly specified otherwise.

The terms "including", "comprising" and variations thereof mean "including but not limited to", unless expressly specified otherwise.

The terms "a", "an" and "the" mean "one or more", unless expressly specified otherwise.

The term "and/or", when such term is used to modify a list of things or possibilities (such as an enumerated list of possibilities) means that any combination of one or more of the things or possibilities is intended, such that while in some embodiments any single one of the things or possibilities may be sufficient in other embodiments two or more (or even each of) the things or possibilities in the list may be preferred, unless expressly specified otherwise. Thus for example, a list of "a, b and/or c" means that any of the following interpretations would be appropriate: (i) each of "a", "b" and "c"; (ii) "a" and "b"; (iii) "a" and "c"; (iv) "b" and "c"; (v) only "a"; (vi) only "b"; and (vii) only "c."

The term "plurality" means "two or more", unless expressly specified otherwise.

The term "herein" means "in the present disclosure, including anything which may be incorporated by reference", unless expressly specified otherwise.

The phrase "at least one of", when such phrase modifies a plurality of things (such as an enumerated list of things) means any combination of one or more of those things, unless expressly specified otherwise. For example, the phrase at least one of a widget, a car and a wheel means either (i) a widget, (ii) a car, (iii) a wheel, (iv) a widget and a car, (v) a widget and a wheel, (vi) a car and a wheel, or (vii) a widget, a car and a wheel.

The phrase "based on" does not mean "based only on", unless expressly specified otherwise. In other words, the phrase "based on" describes both "based only on" and "based at least on".

Each process (whether called a method, algorithm or otherwise) inherently includes one or more steps, and therefore all references to a "step" or "steps" of a process have an inherent antecedent basis in the mere recitation of the term 'process' or a like term. Accordingly, any reference in a claim to a 'step' or 'steps' of a process has sufficient antecedent basis.

When an ordinal number (such as "first", "second", "third" and so on) is used as an adjective before a term, that ordinal number is used (unless expressly specified otherwise) merely to indicate a particular feature, such as to distinguish that particular feature from another feature that is described by the same term or by a similar term. For example, a "first widget" may be so named merely to distinguish it from, e.g., a "second widget". Thus, the mere usage of the ordinal numbers "first" and "second" before the term "widget" does not indicate any other relationship between the two widgets, and likewise does not indicate any other characteristics of either or both widgets. For example, the mere usage of the ordinal numbers "first" and "second" before the term "widget" (1) does not indicate that either widget comes before or after any other in order or location; (2) does not indicate that either widget occurs or acts before or after any other in time; and (3) does not indicate that either widget ranks above or below any other, as in importance or quality. In addition, the mere usage of ordinal numbers does not define a numerical limit to the features identified with the ordinal numbers. For example, the mere usage of the ordinal numbers "first" and "second" before the term "widget" does not indicate that there must be no more than two widgets.

When a single device, component or article is described herein, more than one device, component or article (whether or not they cooperate) may alternatively be used in place of the single device, component or article that is described. Accordingly, the functionality that is described as being possessed by a device may alternatively be possessed by more than one device, component or article (whether or not they cooperate).

Similarly, where more than one device, component or article is described herein (whether or not they cooperate), a single device, component or article may alternatively be used in place of the more than one device, component or article that is described. For example, a plurality of computer-based devices may be substituted with a single computer-based device. Accordingly, the various functionality that is described as being possessed by more than one device, component or article may alternatively be possessed by a single device, component or article.

The functionality and/or the features of a single device that is described may be alternatively embodied by one or more other devices that are described but are not explicitly described as having such functionality and/or features. Thus, other embodiments need not include the described device itself, but rather can include the one or more other devices which would, in those other embodiments, have such functionality/features.

Devices that are in communication with each other need not be in continuous communication with each other, unless expressly specified otherwise. On the contrary, such devices need only transmit to each other as necessary or desirable, and may actually refrain from exchanging data most of the time. For example, a machine in communication with another machine via the Internet may not transmit data to the other machine for weeks at a time. In addition, devices that are in communication with each other may communicate directly or indirectly through one or more intermediaries.

A description of an embodiment with several components or features does not imply that all or even any of such components and/or features are required. On the contrary, a variety of optional components are described to illustrate the wide variety of possible embodiments of the present invention(s). Unless otherwise specified explicitly, no component and/or feature is essential or required.

Further, although process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

Although a process may be described as including a plurality of steps, that does not indicate that all or even any of the steps are essential or required. Various other embodiments within the scope of the described invention(s) include other processes that omit some or all of the described steps. Unless otherwise specified explicitly, no step is essential or required.

Although a product may be described as including a plurality of components, aspects, qualities, characteristics and/or features, that does not indicate that all of the plurality are essential or required. Various other embodiments within the scope of the described invention(s) include other products that omit some or all of the described plurality.

An enumerated list of items (which may or may not be numbered) does not imply that any or all of the items are mutually exclusive, unless expressly specified otherwise. Likewise, an enumerated list of items (which may or may not be numbered) does not imply that any or all of the items are comprehensive of any category, unless expressly specified otherwise. For example, the enumerated list "a computer, a laptop, a PDA" does not imply that any or all of the three items of that list are mutually exclusive and does not imply that any or all of the three items of that list are comprehensive of any category.

Headings of sections provided in this disclosure are for convenience only, and are not to be taken as limiting the disclosure in any way.

"Determining" something can be performed in a variety of manners and therefore the term "determining" (and like terms) includes calculating, computing, deriving, looking up (e.g., in a table, database or data structure), ascertaining, recognizing, and the like.

A "display" as that term is used herein is an area that conveys information to a viewer. The information may be dynamic, in which case, an LCD, LED, CRT, Digital Light Processing (DLP), rear projection, front projection, or the like may be used to form the display. The aspect ratio of the display may be 4:3, 16:9, or the like. Furthermore, the resolution of the display may be any appropriate resolution such as 480i, 480p, 720p, 1080i, 1080p or the like. The format of information sent to the display may be any appropriate format such as Standard Definition Television (SDTV), Enhanced Definition TV (EDTV), High Definition TV (HDTV), or the like. The information may likewise be static, in which case, painted glass may be used to form the display. Note that static information may be presented on a display capable of displaying dynamic information if desired. Some displays may be interactive and may include touch screen features or associated keypads as is well understood.

The present disclosure may refer to a "control system," interface, or program. A control system, interface, or program, as that term is used herein, may be a computer processor coupled with an operating system, device drivers, and appropriate programs (collectively "software") with instructions to provide the functionality described for the control system. The software is stored in an associated memory device (sometimes referred to as a computer readable medium). While it is contemplated that an appropriately programmed general purpose computer or computing device may be used, it is also contemplated that hard-wired circuitry or custom hardware (e.g., an application specific integrated circuit (ASIC)) may be used in place of, or in combination with, software instructions for implementation of the processes of various embodiments. Thus, embodiments are not limited to any specific combination of hardware and software.

A "processor" means any one or more microprocessors, Central Processing Unit (CPU) devices, computing devices, microcontrollers, digital signal processors, or like devices. Exemplary processors are the INTEL PENTIUM or AMD ATHLON processors.

The term "computer-readable medium" refers to any statutory medium that participates in providing data (e.g., instructions) that may be read by a computer, a processor or a like device. Such a medium may take many forms, including but not limited to non-volatile media, volatile media, and specific statutory types of transmission media. Non-volatile media include, for example, optical or magnetic disks and other persistent memory. Volatile media include DRAM, which typically constitutes the main memory. Statutory types of transmission media include coaxial cables, copper wire and fiber optics, including the wires that comprise a system bus coupled to the processor. Common forms of computer-readable media include, for example, a floppy disk, a flexible disk, hard disk, magnetic tape, any other magnetic medium, a CD-ROM, Digital Video Disc (DVD), any other optical medium, punch cards, paper tape, any other physical medium with patterns of holes, a RAM, a PROM, an EPROM, a FLASH-EEPROM, a USB memory stick, a dongle, any other memory chip or cartridge, a carrier wave, or any other medium from which a computer can read. The terms "computer-readable memory" and/or "tangible media" specifically exclude signals, waves, and wave forms or other intangible or non-transitory media that may nevertheless be readable by a computer.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols. For a more exhaustive list of protocols, the term "network" is defined below and includes many exemplary protocols that are also applicable here.

It will be readily apparent that the various methods and algorithms described herein may be implemented by a control system and/or the instructions of the software may be designed to carry out the processes of the present invention.

Where databases are described, it will be understood by one of ordinary skill in the art that (i) alternative database structures to those described may be readily employed, and (ii) other memory structures besides databases may be readily employed. Any illustrations or descriptions of any sample databases presented herein are illustrative arrangements for stored representations of information. Any number of other arrangements may be employed besides those suggested by, e.g., tables illustrated in drawings or elsewhere. Similarly, any illustrated entries of the databases represent exemplary information only; one of ordinary skill in the art will understand that the number and content of the entries can be different from those described herein. Further, despite any depiction of the databases as tables, other formats (including relational databases, object-based models, hierarchical electronic file structures, and/or distributed databases) could be used to store and manipulate the data types described herein. Likewise, object methods or behaviors of a database can be used to implement various processes, such as those described herein. In addition, the databases may, in a known manner, be stored locally or remotely from a device that accesses data in such a database. Furthermore, while unified databases may be contemplated, it is also possible that the databases may be distributed and/or duplicated amongst a variety of devices.

As used herein a "network" is an environment wherein one or more computing devices may communicate with one another. Such devices may communicate directly or indirectly, via a wired or wireless medium such as the Internet, LAN, WAN or Ethernet (or IEEE 802.3), Token Ring, or via any appropriate communications means or combination of communications means. Exemplary protocols include but are not limited to: Bluetooth™, Time Division Multiple Access (TDMA), Code Division Multiple Access (CDMA), Global System for Mobile communications (GSM), Enhanced Data rates for GSM Evolution (EDGE), General Packet Radio Service (GPRS), Wideband CDMA (WCDMA), Advanced Mobile Phone System (AMPS), Digital AMPS (D-AMPS), IEEE 802.11 (WI-FI), IEEE 802.3, SAP, the best of breed (BOB), system to system (S2S), or the like. Note that if video signals or large files are being sent over the network, a broadband network may be used to alleviate delays associated with the transfer of such large files, however, such is not strictly required. Each of the devices is adapted to communicate on such a communication means. Any number and type of machines may be in communication via the network. Where the network is the Internet, communications over the Internet may be through a website maintained by a computer on a remote server or over an online data network including commercial online service providers, bulletin board systems, and the like. In yet other embodiments, the devices may communicate with one another over RF, cable TV, satellite links, and the like. Where appropriate encryption or other security measures such as logins and passwords may be provided to protect proprietary or confidential information.

It will be readily apparent that the various methods and algorithms described herein may be implemented by, e.g., appropriately programmed general purpose computers and computing devices. Typically a processor (e.g., one or more microprocessors) will receive instructions from a memory or like device, and execute those instructions, thereby performing one or more processes defined by those instructions. Further, programs that implement such methods and algorithms may be stored and transmitted using a variety of media (e.g., computer readable media) in a number of manners. In some embodiments, hard-wired circuitry or custom hardware may be used in place of, or in combination with, software instructions for implementation of the processes of various embodiments. Thus, embodiments are not limited to any specific combination of hardware and software. Accordingly, a description of a process likewise describes at least one apparatus for performing the process, and likewise describes at least one computer-readable medium and/or memory for performing the process. The apparatus that performs the process can include components and devices (e.g., a processor, input and output devices) appropriate to perform the process. A computer-readable medium can store program elements appropriate to perform the method.

The present disclosure provides, to one of ordinary skill in the art, an enabling description of several embodiments and/or inventions. Some of these embodiments and/or inventions may not be claimed in the present application, but may nevertheless be claimed in one or more continuing applications that claim the benefit of priority of the present application. Applicants intend to file additional applications to pursue patents for subject matter that has been disclosed and enabled but not claimed in the present application.

The foregoing description discloses only example embodiments of the invention. Modifications of the above-disclosed apparatus, systems and methods which fall within the scope of the invention will be readily apparent to those of ordinary skill in the art.

Accordingly, while the present invention has been disclosed in connection with exemplary embodiments thereof, it should be understood that other embodiments may fall within the spirit and scope of the invention, as defined by the following claims.

The invention claimed is:

1. A method comprising:
   determining a reference value on a first device, wherein the reference value is not an actual or literal indication of status of the first device;
   broadcasting the reference value from the first device;
   connecting the first device to a second device if the second device requests data from the first device;
   transmitting any new data if the second device requests data from the first device;
   generating and broadcasting a new reference value if the first device has new data, wherein the new reference value is not an actual or literal indication of status of the first device;
   broadcasting the reference value from the first device again if the first device does not have new data;
   receiving the reference value in the second device from the first device;
   waiting for the new reference value if the received reference value matches a stored reference value;
   transmitting a request from the second device for new data from the first device if the received reference value does not match the stored reference value;
   receiving new data from the first device into the second device if the received reference value does not match the stored reference value; and
   storing the received reference value as a new stored reference value if the received reference value does not match the stored reference value.

2. The method of claim 1 wherein determining a reference value includes determining a value based upon at least one of a state variable value, a random value, an incremental value, a date/time stamp value, and a data characteristic value.

3. The method of claim 1 wherein broadcasting the reference value from the first device includes broadcasting Bluetooth Low Energy (BLE) advertising data.

4. The method of claim 3 wherein the reference value is included in the BLE advertising data.

5. The method of claim 1 wherein connecting the first device to the second device includes establishing a wireless communications channel between the first device and the second device.

6. The method of claim 1 wherein connecting the first device to the second device includes pairing the first device and the second device.

7. The method of claim 1 wherein the first device is a blood glucose meter (BGM) and the second device is a smart device.

8. A system comprising:
   a first device; and
   a second device,
   wherein the first device includes a controller having memory operative to store instructions executable on the controller, the instructions operative to:
   determine a reference value on the first device, wherein the reference value is not an actual or literal indication of status of the first device,
   broadcast the reference value from the first device,
   connect the first device to the second device if the second device requests data from the first device,
   transmit any new data if the second device requests data from the first device,
   generate and broadcast a new reference value if the first device has new data, wherein the new reference value is not an actual or literal indication of status of the first device, and
   broadcast the reference value from the first device again if the first device does not have new data;
   wherein the second device includes a controller having memory operative to store instructions executable on the controller, the instructions operative to:
   receive the reference value in the second device from the first device,
   wait for the new reference value if the received reference value matches a stored reference value,
   transmit a request from the second device for new data from the first device if the received reference value does not match the stored reference value, receive new data from the first device into the second device if the received reference value does not match the stored reference value, and store the received reference value as a new stored reference value if the received reference value does not match the stored reference value.

9. The system of claim 8 wherein the instruction to determine a reference value includes an instruction to determine a value based upon at least one of a state variable value, a random value, an incremental value, a date/time stamp value, and a data characteristic value.

10. The system of claim 8 wherein the instruction to broadcast the reference value from the first device includes an instruction to broadcast Bluetooth Low Energy (BLE) advertising data.

11. The system of claim 10 wherein the reference value is included in the BLE advertising data.

12. The system of claim 8 wherein the instruction to connect the first device to the second device includes an instruction to establish a wireless communications channel between the first device and the second device.

13. The system of claim 8 wherein the instruction to connect the first device to the second device includes an instruction to pair the first device and the second device.

14. The system of claim 8 wherein the first device is a blood glucose meter (BGM) and the second device is a smart device.

15. A wireless device comprising:
a controller; and
a memory coupled to the controller, the memory operative to store instructions executable on the controller and operative to:

determine a reference value, wherein the reference value is not an actual or literal indication of status of the wireless device;

broadcast the reference value; and connect to a smart device if the smart device requests new data from the wireless device after receiving the broadcast reference value and determining that the broadcast reference value does not match a stored reference value.

16. The wireless device of claim 15 wherein the instruction to determine a reference value includes an instruction to determine a value based upon at least one of a state variable value, a random value, an incremental value, a date/time stamp value, and a data characteristic value.

17. The wireless device of claim 15 further including instructions operative to transfer new data to the smart device if the smart device requests new data from the wireless device.

18. The wireless device of claim 15 wherein the instruction to broadcast the reference value from the wireless device includes an instruction to broadcast Bluetooth Low Energy (BLE) advertising data including the reference value.

19. The wireless device of claim 15 wherein the instruction to connect the wireless device to the smart device includes an instruction to establish a wireless communications channel between the wireless device and the smart device.

20. The wireless device of claim 15 wherein the wireless device is a blood glucose meter.

* * * * *